United States Patent
Ma et al.

(10) Patent No.: US 7,268,358 B2
(45) Date of Patent: Sep. 11, 2007

(54) METHOD OF MODULATING LASER-ACCELERATED PROTONS FOR RADIATION THERAPY

(75) Inventors: Chang-Ming Ma, Huntington Valley, PA (US); Eugene S. Fourkal, Philadelphia, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 11/445,850

(22) Filed: Jun. 1, 2006

(65) Prior Publication Data

US 2007/0034812 A1    Feb. 15, 2007

Related U.S. Application Data

(63) Continuation-in-part of application No. PCT/US04/40724, filed on Dec. 2, 2004.

(60) Provisional application No. 60/526,436, filed on Dec. 2, 2003.

(51) Int. Cl.
     *H01J 37/08*      (2006.01)
     *G21K 5/10*      (2006.01)

(52) U.S. Cl. .............. 250/492.3; 250/492.21; 250/492.22; 250/492.23; 250/396 ML; 250/396 R; 250/505.1; 250/306; 250/307; 250/309

(58) Field of Classification Search .......... 250/492.21, 250/492.22
See application file for complete search history.

(56) References Cited

U.S. PATENT DOCUMENTS

| | | | |
|---|---|---|---|
| 3,555,332 A | 1/1971 | Schroeder et al. | 313/63 |
| 3,786,359 A | 1/1974 | King | 328/233 |
| 4,297,191 A | 10/1981 | Chen | 204/193 |
| 6,043,488 A * | 3/2000 | Bahatt et al. | 250/294 |
| 6,534,764 B1 * | 3/2003 | Verentchikov et al. | 250/287 |
| 6,639,234 B1 | 10/2003 | Badura et al. | 250/492.3 |
| 6,642,525 B2 * | 11/2003 | Kienzle et al. | 250/396 ML |
| 6,670,618 B1 | 12/2003 | Hartmann et al. | 250/491.1 |
| 6,680,480 B2 | 1/2004 | Schoen | 250/423 R |
| 6,736,831 B1 | 5/2004 | Hartmann et al. | 607/1 |
| 6,745,072 B1 | 6/2004 | Badura et al. | 607/2 |
| 6,799,068 B1 | 9/2004 | Hartmann et al. | 607/2 |
| 6,885,014 B2 * | 4/2005 | Benveniste | 250/492.21 |
| 6,897,457 B1 | 5/2005 | Holmes et al. | 250/492.21 |
| 6,906,338 B2 | 6/2005 | Tajima | 250/505.1 |
| 6,998,625 B1 * | 2/2006 | McKenna et al. | 250/492.21 |
| 2002/0084422 A1 * | 7/2002 | Kienzle et al. | 250/396 ML |
| 2003/0141460 A1 | 7/2003 | Kraft | 250/492.1 |
| 2005/0029471 A1 * | 2/2005 | Kraft et al. | 250/492.1 |
| 2005/0061997 A1 * | 3/2005 | Benveniste | 250/492.21 |
| 2006/0145088 A1 * | 7/2006 | Ma | 250/396 ML |
| 2006/0219944 A1 * | 10/2006 | Benveniste | 250/492.1 |
| 2007/0034812 A1 * | 2/2007 | Ma et al. | 250/492.21 |

FOREIGN PATENT DOCUMENTS

WO    WO 2005/057738 A2    6/2005

\* cited by examiner

*Primary Examiner*—Robert Kim
*Assistant Examiner*—Bernard Souw
(74) *Attorney, Agent, or Firm*—Woodcock Washburn LLP

(57) ABSTRACT

Methods of optimizing a laser-accelerated proton radiation dose to a targeted region are disclosed. Disclosed methods include providing a plurality of modulated polyenergetic proton beamlets and irradiating the targeted region with the plurality of modulated beamlets.

38 Claims, 20 Drawing Sheets

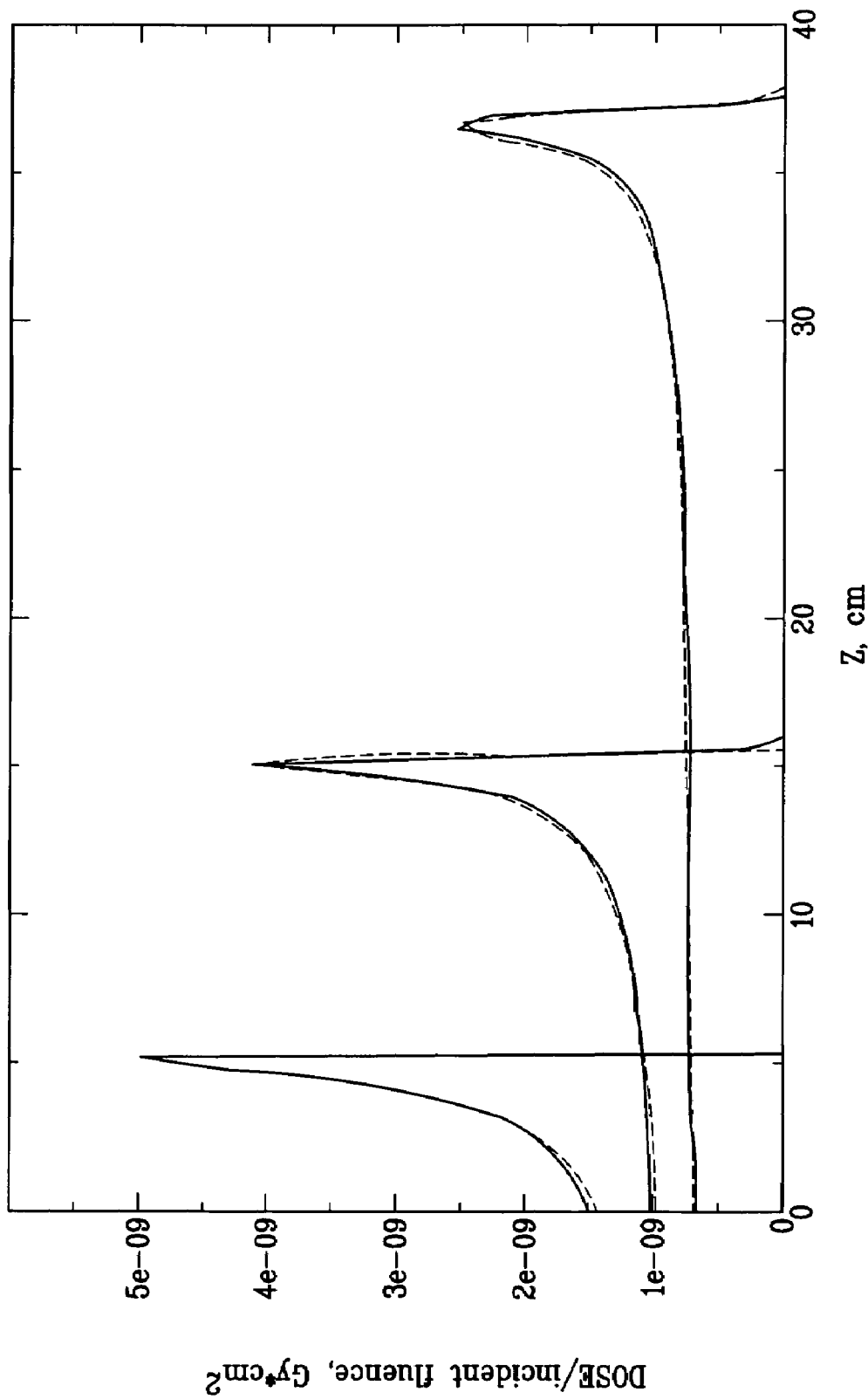

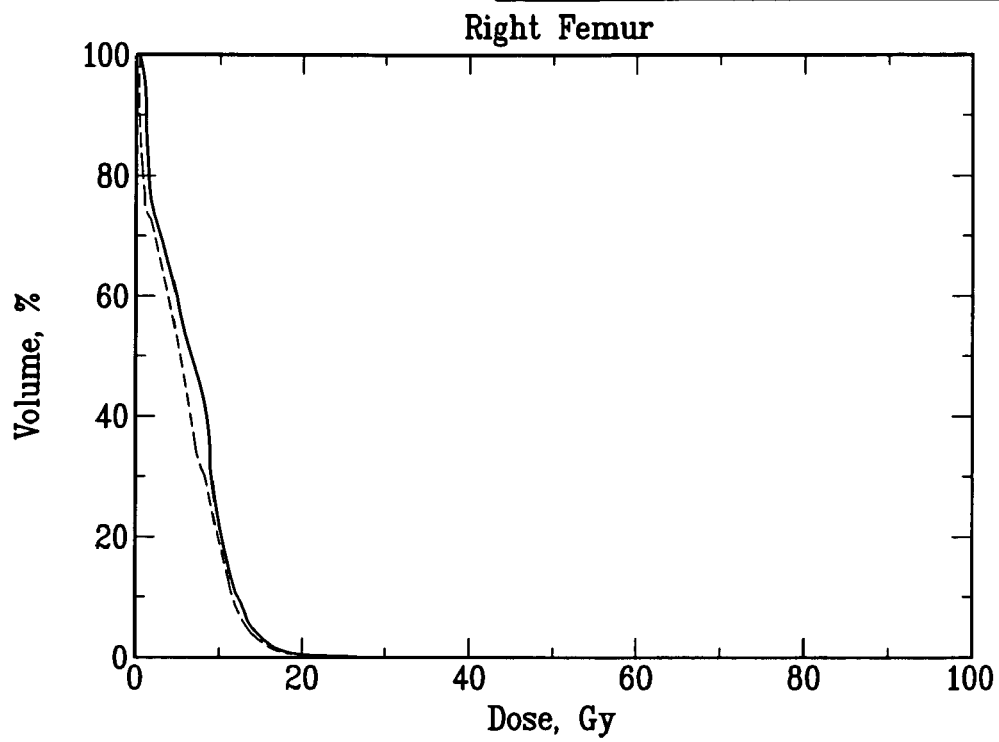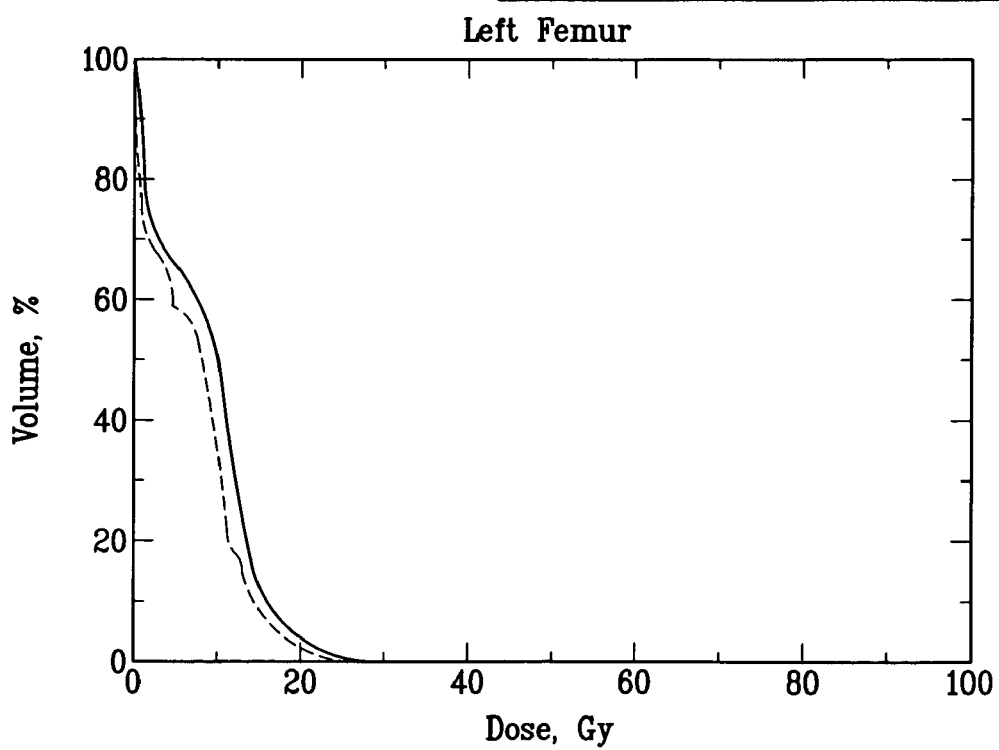
FIG. 10

METHOD OF MODULATING LASER-ACCELERATED PROTONS FOR RADIATION THERAPY

CROSS REFERENCE TO RELATED APPLICATIONS

This application is a continuation-in-part of International Patent Application No. PCT/US2004/040724, filed Dec. 2, 2004, which claims the benefit of U.S. provisional patent application Ser. No. 60/526,436, filed Dec. 2, 2003, and International Patent Application No. PCT/US2004/017081, filed Jun. 2, 2004. The entirety of each of these applications is incorporated by reference herein.

GOVERNMENT RIGHTS

The work leading to the disclosed invention was funded in whole or in part with Federal funds from the Department of Health and Human Services, the National Institutes of Health, and the Department of Defense. The Government may have certain rights in the invention under NIH contract number CA78331, DHHS contract number C76HF00691-01-00, and DOD contract number PC030800.

FIELD OF THE INVENTION

The invention relates to methods useful for prescribing and modulating high energy positive ions for use in ion radiation therapy. In particular, the invention relates to methods useful for prescribing and modulating high energy protons for use in proton radiation therapy. The invention also relates to treatment optimization methods for providing therapeutic radiation doses.

BACKGROUND OF THE INVENTION

One aim of radiation therapy is to deliver a prescribed dose of radiation to a target volume while minimizing the dose to surrounding healthy tissues. The extent to which this can be accomplished depends on many factors including the beam dosimetric characteristics and the delivery method. The use of proton beams provides the possibility of superior dose conformity to the treatment target as well as a better normal tissue sparing as a result of the Bragg peak effect (Wilson, R. R., "Radiological uses of fast protons", *Radiology*, 1946, 487-495). While photons show high entrance dose and slow attenuation with depth, protons have a very sharp peak of energy deposition as a function of beam penetration. As a consequence, it is possible for a larger portion of the incident proton energy to be deposited within or very near a three-dimensional ("3D") planning target volume ("PTV"), thus avoiding radiation-induced injury to surrounding normal tissues.

Despite the dosimetric superiority characterized by the sharp Bragg peak, utilization of proton therapy has lagged behind that of photon therapy. For example, the operating regime (the total operating cost for accelerator maintenance, energy consumption, and technical support) for proton accelerators is at least an order of magnitude higher than electron/X-ray medical accelerators. Currently, proton therapy centers utilize cyclotrons and synchrotrons (Jongen, A. A., "Proton therapy system for MGH's NPTC: equipment description and progress report", *Cyclotrons and their Applications*, ed J. C. Cornell (New Jersey: World Scientific), 1996, pp. 606-609; Cole, F. T. "Accelerator Considerations in the Design of a Proton Therapy Facility", *Particle Acceleration Corp. Rep.*, 1991). Despite a somewhat limited number of clinical cases from these facilities, treatment records have shown encouraging results particularly for well localized radio-resistant lesions (Fuss, M., et al., "Proton radiation therapy (PRT) for pediatric optic pathway gliomas: Comparison with 3D planned conventional photons and a standard photon technique", *Int. J. Radiation Oncology Biol. Phys.*, 1999, 1117-1126; Slater, J., et al., "Conformal proton therapy for prostate carcinoma", *Int. J. Radiation Oncology Biol. Phys.*, 1998, 299-304; Shipley, W., et al., "Advanced prostate cancer: the results of a randomized comparative trial of high dose irradiation boosting with conformal protons compared with conventional dose irradiation using photons alone", *Int. J Radiation Oncology Biol. Phys.*, 1995, 3-12; Kjellberg, R. N., Stereotactic Bragg Peak Proton Radiosurgery for Cerebral Arteriovenous Malformations *Ann Clin. Res. Supp.* 47, 1986, 17-25). However, the availability of proton radiation therapy needs to be greatly improved. Making available a compact, flexible, and cost effective proton therapy system would enable the widespread use of this superior beam modality and therefore bring significant advances in the management of cancer.

For a long time proton therapy has led the way in delivering precise, conformal radiation therapy and in many comparative studies has shown improved localization of dose as compared to conventional photon techniques (Archambeau, J. O., et al., 1992, "Role of proton beam irradiation in treatment of pediatric CNS malignancies", *Int. J. Radiation Oncology Biol. Phys.* 287-94; Slater, J. D., et al., "The potential for proton beam therapy in locally advanced carcinoma of the cervix", *Int. J Radiation Oncology Biol. Phys.*, 1992, 343-47; Slater, J. M., et al., "Carcinoma of the tonsillar region: potential for use of proton beam therapy", *Int. J. Radiation Oncology Biol. Phys.*, 1992, 311 -19; Tatsuzaki, H., et al., "Comparative treatment planning: proton vs x-ray beams against glioblastoma multiform", *Int. J. Radiation Oncology Biol. Phys.*, 1991 265-73, "Tatsuzaki 1991a"; Tatsuzaki, H., et al. "3-d comparative study of proton vs. x-ray radiation therapy for rectal cancer", *Int. J. Radiation Oncology Biol. Phys.*, 1991, 369-74, "Tatsuzaki 1991b; Lee, M., et al., "A comparison of proton and megavoltage x-ray treatment planning for prostate cancer", *Radiother. Oncol.*, 1994, 239-53; Miralbell, R., et al. "Potential reduction of the incidence of radiation-induced second cancers by using proton beams in the treatment of pediatric tumors", *Int. J. Rad. Onc. Biol. Phys.*, 2002, 824-829). In recent years, the planning and delivery of x-rays has improved considerably so that the gap between conventional proton techniques (superposition of proton fields with uniform planar fluence) and x-ray methods has significantly decreased. The main pathway of research has been toward the optimization of individual beamlets and the calculation of optimal intensity distributions (for each beamlet) for intensity modulated treatments. Lomax, A. J., et al. ("A treatment planning inter-comparison of proton and intensity modulated photon radiotherapy", *Radiother. Oncol.*, 1999, 257-71, "Lomax 1999a") performed comparative studies between standard photon, intensity-modulated photon and proton plans as applied to different lesion sites and found that for the majority of cases proton plans (with 2-3 field arrangements) provided an advantage by reducing both the mean dose and $V_{50}$ (volume of the structure irradiated to 50% of the target dose) for all organs at risk stemming from the advantageous physical characteristics of protons. On the other hand, there was an example of acinus cell carcinoma in which the target volume was relatively large (350 cc) and partially wrapped around the brain stem. The results of this case demonstrated that intensity modulated (IM) photon plan yielded superior sparing of the brain stem at almost all dose levels. The advantage of IM photons over conventional protons for this particular case does not seem to emanate from the difference in dosimetric characteristics between both modalities. Instead, this advantage seems to be related to the advantage of inverse planning methods over the forward planning methods used for the proton plans in this study. The implementation of the inverse planning techniques into proton therapy has somewhat lagged behind those for photon beam modality. This was apparently due to the limitations in the initial design of the beam delivery methods in conventional proton accelerators. With the advent of three-dimensional spot scanning technique, the implementation of intensity modulation for conventional proton accelerators has been enabled. Recent clinical findings (Lomax, A. J., "Potential role of intensity-modulated photons and protons in the treatment of the breast and regional nodes", *Int. J Rad. Oncol. Biol. Phys.*, 2003, 785-792, "Lomax et al. 2003a"; Lomax, A. J., et al., "Intensity modulation in radiotherapy: photons versus protons in the paranasal sinus", *Radiother. Oncol.*, 2003, 11-18, "Lomax et al. 2003b") suggest that the employment of optimization methods into proton therapy will further improve dose distribution within the target and sparing of the critical structures as compared to IM photons.

Intensity modulation applied to conventional photon beams implies the modulation of its intensity in the plane perpendicular to the beam's propagation direction. This suggests that there is no control over the photon depth dose distribution, preset by the energy spectrum of photons coming out of the accelerator's head. Unlike photons, the depth dose distribution for proton beams can be modulated in such a way as to give SOBP along the target's depth dimension. This is used in conventional proton beam delivery methods in which range shifters are implemented to modulate initially monoenergetic proton beam to give SOBP (Moyers, M., "Proton therapy", *The Modern Technology of Radiation Oncology*, ed J Van Dyk, Medical Physics Publishing, Madison, 1999). In conventional proton beam delivery systems the modulation of the Bragg peak intensity is such that the depth-dose distribution for any single field is flat, with multiple field plans calculated by the simple weighted addition of homogeneous single field dose distributions (Lomax. A. J., et al. "3D treatment planning for conformal proton therapy by spot scanning *Proc. 19th L H Gray Conference*, ed Faulkner, K., et al., (London: BIR publishing), 1999, pp. 67-71, "Lomax 1999b"). This differs from intensity modulation for photons, where a number of individually inhomogeneous fields are used in such a way as to achieve a homogeneous dose distribution within the target, simultaneously reducing the dose to the normal tissues/critical structures. In 1999, Lomax earlier defined a 2.5D intensity modulation method (Lomax, A., "Intensity modulation methods for proton radiotherapy", *Phys. Med. Biol.*, 1999, 185-205, "Lomax 1999c"). The full 3D delivery method described by Brahme et al. ("Optimization of proton and heavy ion therapy using an adaptive inversion algorithm" *Radiother. Oncol.* 1989, 189-197), and more recently by Carlsson et al. ("Monte Carlo and analytical calculation of proton pencil beams for computerized treatment plan optimization", *Phys. Med. Biol.*, 1997, 1033-53) exploits the 3D localization of dose in the Bragg peak by intensity modulating individual narrow beam Bragg peaks in three dimensions.

Laser acceleration was first suggested in 1979 for electrons (Tajima, T., et al., "Laser electron accelerator", *Phys. Rev Lett.*, 1979, 267-270) and rapid progress in laser-electron acceleration began in the 90's after chirped pulse amplification ("CPA") was invented (Strickland, D., et al., "Compression of amplified chirped optical pulses", *Opt. Comm.*, 1985, 219-221) and convenient high fluence solid-state laser materials such as Ti:sapphire were discovered and developed. The first experiment that has observed protons generated with energies much beyond several MeV (58 MeV) is based on the petawatt Laser at Lawrence Livermore National Laboratory (Key, M. H., et al. "Studies of the Relativistic Electron Source and related Phenomena in Petawatt Laser Matter Interactions", *First International Conference on Inertial Fusion Sciences and Applications,* 1999; Snavely, R. A., et al. "Intense high energy proton beams from Petawatt Laser irradiation of solids", *Phys. Rev. Lett.,* 2000, 2945-2948). Until then there had been several experiments that observed protons of energies up to I or 2 MeV (Maksimchuk, A., et al., "Forward Ion acceleration in thin films driven by a high intensity laser", *Phys. Rev. Lett.,* 2000, 4108-4111). Another experiment at the Rutherford-Appleton Laboratory in the U.K. has been reported recently with proton energies of up to 30 MeV (Clark, E. L., et al., "Energetic heavy ion and proton generation from ultraintense laser-plasma interactions with solids", *Phys. Rev. Lett.,* 2000, 1654-1657). The mechanism for proton acceleration is well studied. It has long been understood that ion acceleration in laser-produced plasma relates to the hot electrons (Gitomer, S. J., et al., "Fast ions and hot electrons in the laser-plasma interaction" *Phys. Fluids,* 1986, 2679-2686). A laser pulse interacting with the high-density hydrogen-rich material (plastic, water vapor on the surface of the metal foil) ionizes it and subsequently interacts with the created plasma (collection of free electrons and ions). The commonly recognized effect responsible for ion acceleration is charge separation in the plasma due to high-energy electrons, driven by the laser inside the foil (Maksimchuk et al. 2000; Yu, W. et al., "Electron acceleration by a short relativistic laser pulse at the front of solid targets", *Phys. Rev. Lett.,* 2000, 85, 570-573) or/and an inductive electric field as a result of the self-generated magnetic field (Sentoku, Y., et al., "Bursts of Superreflected Laser Light from Inhomogeneous Plasmas due to the Generation of Relativistic Solitary Waves", *Phys. Rev. Lett.,* 2000, 3434-3437), although a direct laser-ion interaction has been discussed for extremely high laser intensities ~$10^{22}$ W/cm$^2$ (Bulanov, S. V., et al., "Generation of Collimated Beams of Relativistic Ions in Laser-Plasma Interactions", *JETP Letters,* 2000, 407-411).

Using numerical simulations (Fourkal, E., et al., "Particle in cell simulation of laser-accelerated proton beams for radiation therapy", *Med. Phys.,* 2002, 2788-98), the laser/foil parameter range was investigated that can lead to effective proton acceleration. It was found that thin foils (0.5-1 microns thick) with electron densities of $n_c = 5 \times 10^{22}$ cm$^{-3}$ and laser pulse intensity I=$10^{21}$ W/cm$^2$ and length L=50 femtosecond are amenable to effective proton acceleration capable of producing protons with energies 200 MeV and higher. In the previous experimental investigations the thickness of foils was tens and sometimes hundreds of microns with laser pulse lengths of several hundred femtoseconds, leading to lower proton energies. Maximizing the proton energy by irradiating thin foils (less than 1 micrometer thick) with ultrashort high-intensity lasers is an area currently under development.

Simulations of the laser acceleration of protons have been reported in Fourkal et al. (2002). It was shown that due to the broad energy spectrum of the accelerated protons, it is very difficult to use laser-accelerated protons for therapeutic treatments without prior proton energy selection. Once energy selection is achieved, it is possible to give a homogeneous dose distribution through the so-called spread out Bragg's peak (SOBP). The particle selection system capable of yielding protons with a required energy spectrum and intensity has been studied by Fourkal et al. (2003).

The inventions provided herein can be used with the compact, flexible and cost-effective laser-accelerated proton therapy systems as described in (Fourkal et al. 2002; Fourkal, E., et al., "Particle selection for laser-accelerated proton therapy feasibility study", Med. Phys., 2003, 1660-70; Ma, C.-M, et al. "Laser Accelerated proton beams for radiation therapy", Med. Phys., 2001, 1236). These systems are based upon several technological developments: (1) laser-acceleration of high-energy protons, and (2) compact system design for particle (and energy) selection and beam collimation. Related systems, devices, and methods are disclosed in International Patent Application No. PCT/US2004/017081, "High Energy Polyenergetic Ion Selection Systems, Ion Beam Therapy Systems, and Ion Beam Treatment Centers", filed on Jun. 02, 2004, the entirety of which is incorporated by reference herein. For example, FIG. 17 of the PCT/US2004/017081 application (and reproduced herein as FIG. 1a) depicts a laser-accelerated polyenergetic positive ion beam therapy system, further details of which can be found in that application. Likewise, FIG. 41 of the PCTIUS2004/017081 application (and reproduced herein as FIG. 1b) depicts a sectional view of a laser-accelerated high energy polyenergetic positive ion therapy system, further details of which can be found in that application. Such systems provide a way for generating small beamlets of polyenergetic protons, which can be used for irradiating a targeted region (e.g., tumors, lesions and other diseased sites) to treat patients.

Treatment strategies have also been described, for example FIG. 43 of the PCT/US2004/017081 application (and reproduced herein as FIG. 1c) depicts a flow chart of a method of treating a patient using polyenergetic high energy positive ions, further details of which can be found in that application. The disclosed treatment strategies include determining dose distributions of a plurality of therapeutically suitable high energy polyenergetic positive ion beams for irradiating a targeted region and delivering a plurality of therapeutically suitable high energy polyenergetic positive ion beams (i.e., beamlets) to the targeted region. Although determining dose distributions are provided in the PCT/US2004/017081 application, further improvements are needed in optimizing beamlet treatment plans that maximize radiation to targeted regions while minimizing radiation to surrounding critical organs, tissues and structures. Accordingly, one aspect of the present invention provides methods for optimizing polyenergetic proton beamlet treatment plans that maximize polyenergetic proton radiation to targeted regions while minimizing radiation to surrounding critical organs, tissues and structures.

SUMMARY OF THE INVENTION

The present invention provides methods and systems for optimizing polyenergetic proton beamlet treatment plans that maximize polyenergetic proton radiation to targeted regions while minimizing radiation to surrounding critical organs, tissues and structures.

The present invention also provides methods of generating a positive ion beam sequence for providing a prescriptive dose of high energy polyenergetic positive ions to a target volume, comprising the steps of:
  a) providing a plurality of beam angles, plan prescription, and dose constraints;
  b) providing a plan optimization process based on a beam scanning sequence;
  c) applying said beam scanning sequence to said beam angles, plan prescription and dose constraints to generate plan optimization results;
  d) comparing the plan optimization results to the plan prescription; and
  e) modulating the beam scanning sequence and iteratively repeating steps b), c) and d) until the plan optimization results are acceptable.

The present invention further provides methods of providing a prescriptive dose of high energy polyenergetic positive ions to a target volume, comprising the steps of:
  a) providing a plurality of beam angles, plan prescription, and dose constraints;
  b) providing a plan optimization process based on a beam scanning sequence;
  c) applying said beam scanning sequence to said beam angles, plan prescription and dose constraints to generate plan optimization results;
  d) comparing the plan optimization results to the plan prescription;
  e) modulating the beam scanning sequence and iteratively repeating steps b), c) and d) until the plan optimization results are acceptable; and
  f) irradiating the target volume with a plurality of beamlets according to the plan optimization results.

The present invention also provides methods of providing a polyenergetic proton radiation dose to a targeted region, comprising providing a plurality of modulated polyenergetic proton beamlets, wherein each of the beamlets is modulated, individually, according to at least one of: beamlet energy distribution, beamlet intensity, beamlet direction, beamlet area, or beamlet shape; and irradiating the target with the plurality of modulated polyenergetic proton beamlets, wherein the plurality of modulated polyenergetic proton beamlets maximizes the proton radiation dose to the target and minimizes the proton radiation dose to areas external to the target.

The present invention also provides methods for optimizing the combination and modulation of laser-accelerated protons for use in radiation therapy. Two features of proton dosimetric characteristics, the controllability of the target depth direction and the sharp decrease of the radiation dose beyond the effective Bragg peak, are combined with beamlet optimization techniques to provide a highly conformal dose distribution within a planning target volume ("PTV") that maximizes healthy tissue sparing regardless of the location of the disease.

The present invention also provides methods of providing a positive ion radiation dose to a targeted region, comprising providing a plurality of modulated polyenergetic positive ion beamlets, and irradiating the targeted region with the plurality of modulated polyenergetic positive ion beamlets.

The present invention further provides methods of providing a positive ion radiation dose to a targeted region, comprising providing a plurality of modulated polyenergetic positive ion beamlets, and irradiating the targeted region with the plurality of modulated polyenergetic positive ion beamlets.

The present invention further provides methods of providing a proton radiation dose to a targeted region, comprising the steps of providing a plurality of modulated polyenergetic proton beamlets, wherein each of the polyenergetic beamlets is modulated, individually, according to at least one of: beamlet energy distribution, beamlet intensity, beamlet direction, beamlet area, or beamlet shape; and irradiating said targeted region with the plurality of modulated polyenergetic proton beamlets, wherein the plurality of modulated polyenergetic proton beamlets maximizes the proton radiation dose to the targeted region and minimizes the proton radiation dose to areas external to the targeted region.

The present invention also provides methods of providing a prescriptive dose to a targeted region in a patient, comprising the steps of providing a plurality of polyenergetic proton beamlets, and modulating the polyenergetic proton beamlets, wherein the modulating gives rise to an acceptable dose distribution to the targeted region according to the prescriptive dose in both longitudinal and lateral directions relative to the beamlets.

The present invention also provides methods and systems of providing a positive ion radiation dose, comprising providing a plurality of polyenergetic positive ion beamlets, and modulating the polyenergetic positive ion beamlets, wherein the modulating gives rise to a desired dose distribution based on a prescribed dose to a target in both longitudinal and lateral directions relative to said beamlets.

The present invention additionally provides methods of providing intensity modulated proton therapy to a targeted region in a patient. These methods include the steps of providing a plurality of high energy positive ion beamlets, modulating at least one of the high energy positive ion beamlets in depth relative to the patient to provide a depth-modulated beamlet, modulating at least one of the depth-modulated beamlets in a lateral direction relative to the patient to provide a lateral-modulated beamlet, and irradiating the targeted region with at least one of the lateral-modulated beamlets to the patient.

The methods are applied to a prostate lesion as an exemplary disease site. The results show how laser-accelerated intensity modulated proton therapy (IMPT) can be optimally used. The methods described herein can be readily applied to any other type of disease site.

Other aspects of the present invention will be apparent to those skilled in the art in view of the detailed description of the invention as provided herein.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods and instrumentalities disclosed. In the drawings:

FIG. 2 compares proton depth dose distributions calculated using GEANT3 and the track repeating technique. The solid lines represent depth dose distributions for protons with energies 80 MeV, 150 MeV and 250 MeV calculated using the track repeating technique and the dashed lines represent depth dose distributions calculated using GEANT3 simulation tool.

FIG. 10 provides dose-volume histograms for the right and left femoral heads. The plan was normalized to 95% of the PTV's volume, which receives 100% of the prescription dose of 74 Gy.

DETAILED DESCRIPTION OF ILLUSTRATIVE EMBODIMENTS

Figure 1A:
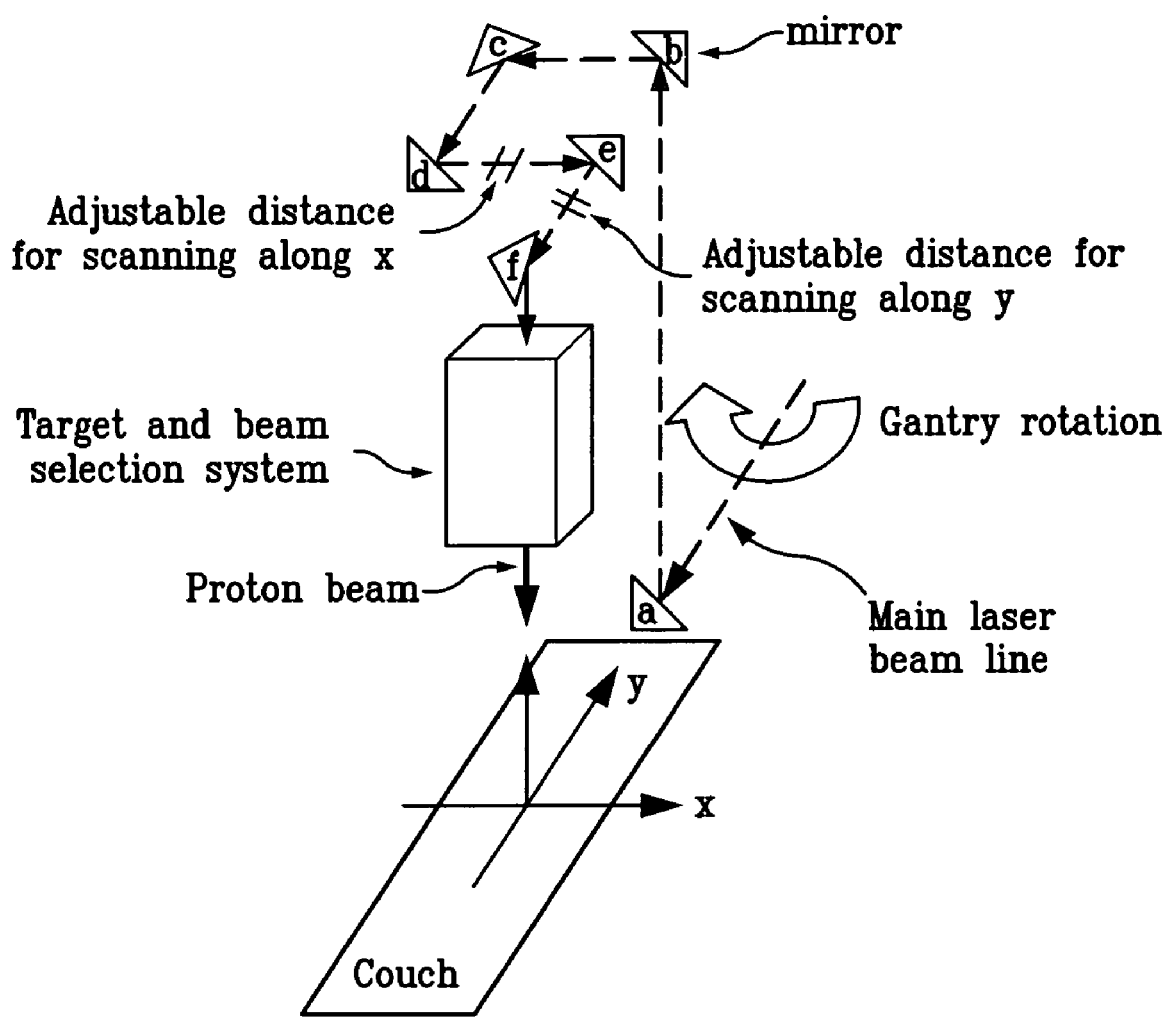
FIG. 1a shows a schematic diagram of a laser-accelerated positive ion beam therapy unit (the laser is not shown) having a laser beam line and beam scanning mechanism of a laser-accelerated proton therapy system of the invention.

At least a portion of the following abbreviations and acronyms are used herein:

CORVUS a treatment optimization system for photon IMRT from NOMOS
CPA chirped pulse amplification
CT computer-aided tomography
D dimension
DICOM Digital Imaging and Communications in Medicine
DICOM RT DICOM Radiation Therapy Supplement
DVH dose-volume histogram
EIMPT energy- and intensity-modulated proton therapy
EGS4 Electron Gamma Shower (version 4) Monte Carlo code system
FWHM Full Wave Half Maximum
GEANT(3) a Monte Carlo system for radiation (proton, neutron, etc) simulation
IMPT Intensity Modulated Proton Therapy
IMRT intensity-modulated radiation therapy
IMXT Intensity Modulated X-ray Therapy (e.g., as provided using a linear accelerator ("linac") photon beam)
JanUSP a high power ($10^{19}$-$10^{21}$ W/cm$^2$) laser at LLNL
LLNL Lawrence Livermore National Laboratory
LLUMC Loma Linda University Medical Center, Loma Linda, Calif.
MCDOSE an EGS4 user-code for dose calculation in a 3-D geometry
MGH Massachusetts General Hospital, Boston, Mass.
MLC multileaf collimator
NOMOS NOMOS Corp., Sewickley, Pa.
NTCP normal tissue complication probability
PC personal computer
PIC particle-in-cell (simulation technique for laser plasma physics)
PMC primary monitor chamber
PSA prostate-specific antigen
PTV planning target volume
PTRAN a Monte Carlo code system for proton transport simulation
RBE relative biological effectiveness
RTP radiotherapy treatment planning
SMC secondary monitor chamber
SOBP spread out Bragg peak (for proton/ion beams)
SSD source-surface distance
TCP tumor control probability
MeV million electron volts
GeV billion electron volts
T Tesla As used herein, the term "protons" refers to the atomic nuclei of hydrogen ($H^1$) having a charge of +1.

As used herein, the term "positive ions" refers to atoms and atomic nuclei having a net positive charge.

As used herein, the term "polyenergetic" refers to a state of matter being characterized as having more than one energy level.

As used herein, the term "high energy" refers to a state of matter being characterized as having an energy level greater than 1 MeV.

As used herein, the term "beamlet" refers to a portion of a high energy polyenergetic positive ion beam that is spatially separated, or energetically separated, or both spatially and energetically separated.

As used herein, the term "plurality" means more than one.

The terms "primary collimator", "primary collimation device", "initial collimator", and "initial collimation device" are used interchangeably herein.

As used herein, the verb "to modulate" means to vary, change, or alter the properties of something in a controlled fashion.

As used herein, the adjective "modulated" refers to something in which the properties have been varied, changed, or altered in a controlled fashion.

The terms "energy modulation system" and "aperture" are used interchangeably when it is apparent that the aperture referred to is capable of modulating a spatially separated high energy polyenergetic positive ion beam.

The terms "laser target" and "target" typically refer to different things. The term "laser target" typically refers to the target material that is exposed to a high intensity laser pulse for generating high energy polyenergetic positive ions. The term "target" alone is synonymous with the term "targeted region", which refers to the tissue targeted in a patient for irradiation with positive ions.

As used herein, the term "targeted volume," "target volume," "target region," and "targeted region" are synonymous with each other.

As used herein, the term "longitudinal direction relative to the beamlet" means along the incident direction of the protons or positive ions.

As used herein, the term "lateral direction relative to the beamlet" means lateral to the incident direction of the protons or positive ions.

As used herein, the term "voxel" means volume element.

As used herein, the term "modulating proton beamlets" means that individual beamlets may have different energy spectra and intensities or weights.

As used herein, the phrase "prescriptive dose to the target" means the physical or biologically equivalent dose to the target volume of a targeted region (i.e., taking into account the difference in RBE between photons and light ions) prescribed by a radiation oncologist as considered to be necessary for the treatment.

As used herein, the term "isodose" refers to the display of information that connects points of equal dose values.

As used herein, the terms "field" and "port" correspond to an incident beam direction, determined by a combination of the gantry angle and couch angle. A field can be sub-divided into sub-fields called "beamlets" or "apertures".

All ranges disclosed herein are inclusive and combinable.

In certain embodiments of the present invention, a physical (or biologically equivalent) dose of proton radiation for irradiating a targeted region is determined. Radiotherapy is typically a local (i.e., regional) therapy mode that uses a certain dose (i.e., a desired prescription dose) to achieve local control. Suitable desired prescriptive doses can be inhomogeneous (i.e., nonhomogeneous) but are typically homogeneous. As used herein, a homogeneous dose (i.e., a homogeneous prescriptive dose) provides that no tumor cells in the target volume will survive the treatment that would otherwise result in a recurrence of the tumor. Higher doses in part of the target volume (e.g., hot spots) typically do not improve local control, since a tumor cell typically is not killed twice. Lower doses in part of the target volume (e.g., cold spots) may result in the survival of some tumor cells leading to tumor recurrence. In addition, high doses to the targeted region typically results in higher doses to the nearby critical structures/organs. In this regard, certain aspects of the methods of the present invention determine an optimal selection of proton beamlets needed to deliver homogenous (i.e., optimally desired prescriptive, or uniform) doses to a targeted region. Accordingly, the selection of proton beamlets that are determined preferably minimize as much as possible the presence of both hot spots and cold spots that typically accompany inhomogeneous doses.

In certain embodiments, the desired dose distribution may be an inhomogeneous dose since with the development of radiotherapy techniques such as image guided therapy. In this embodiment, inhomogeneous prescriptive doses can be used to treat different parts of a tumor with different doses. The choice of doses will depend, for example, depending on the tumor cell density, biological and biochemical environment.

Figure 1B:
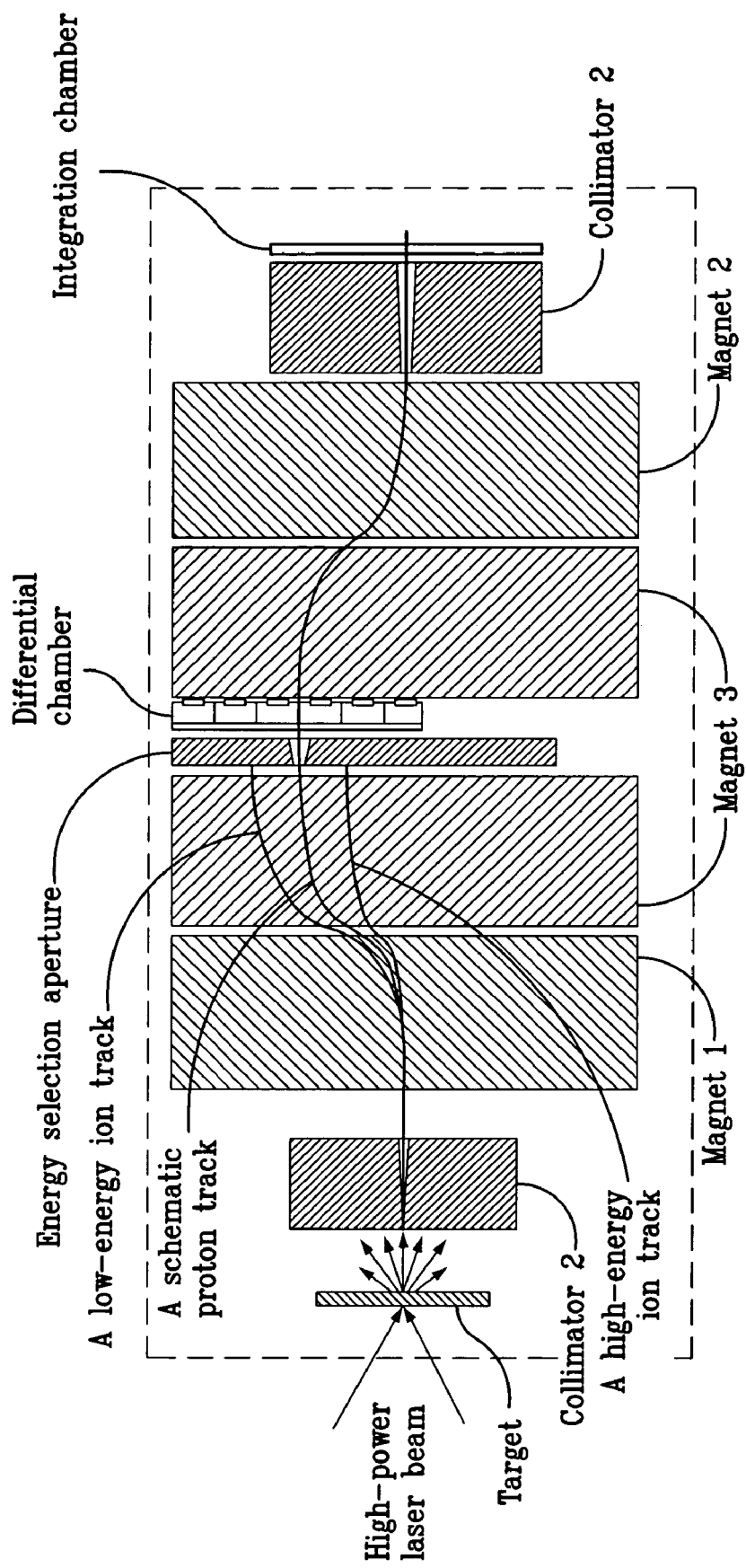
FIG. 1b depicts a sectional view of a laser-accelerated high energy polyenergetic positive ion therapy system.
Figure 1C:
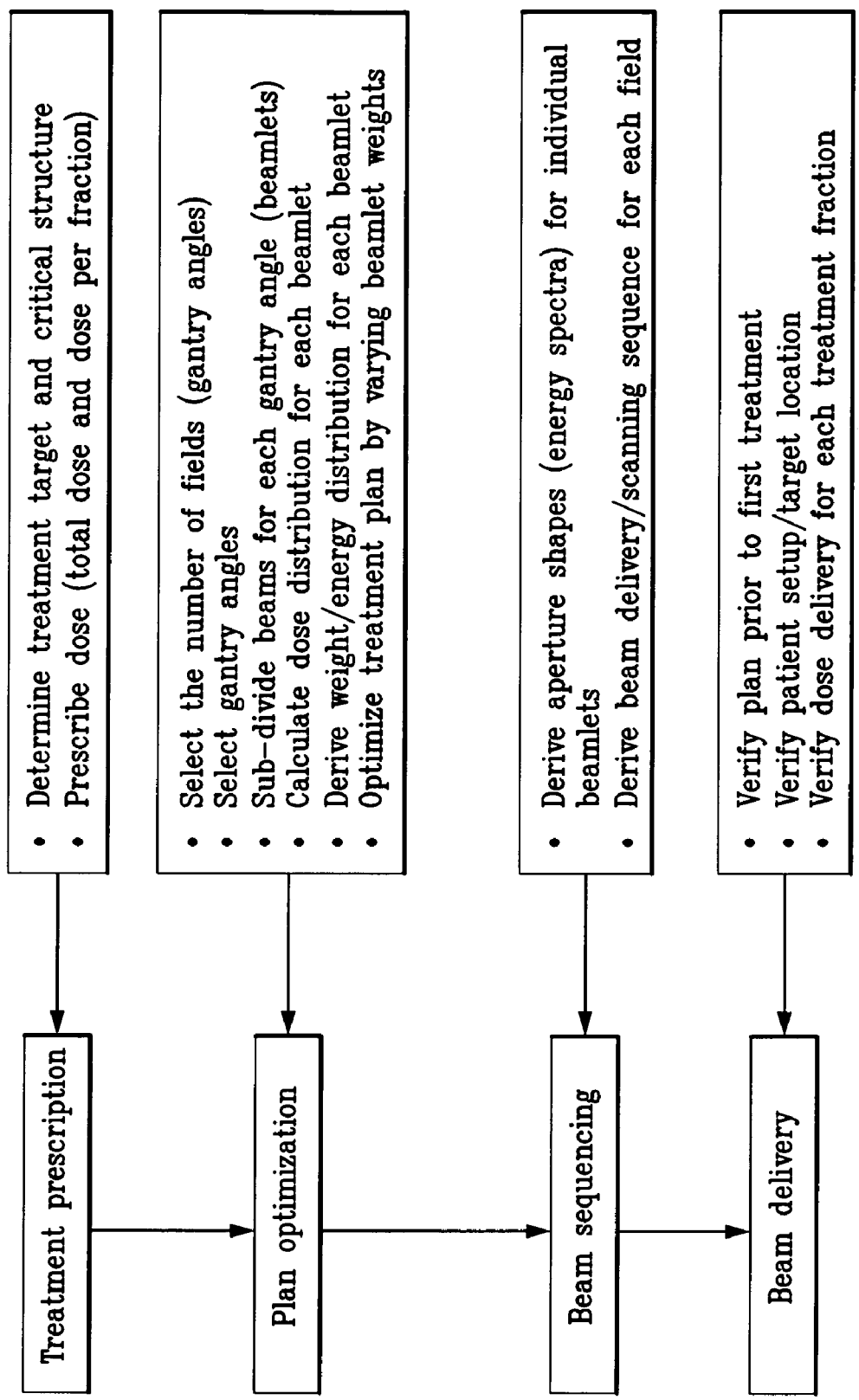
FIG. 1c depicts a flow chart of an embodiment of a method of treating a patient using polyenergetic high energy positive ions.
Figure 1D:
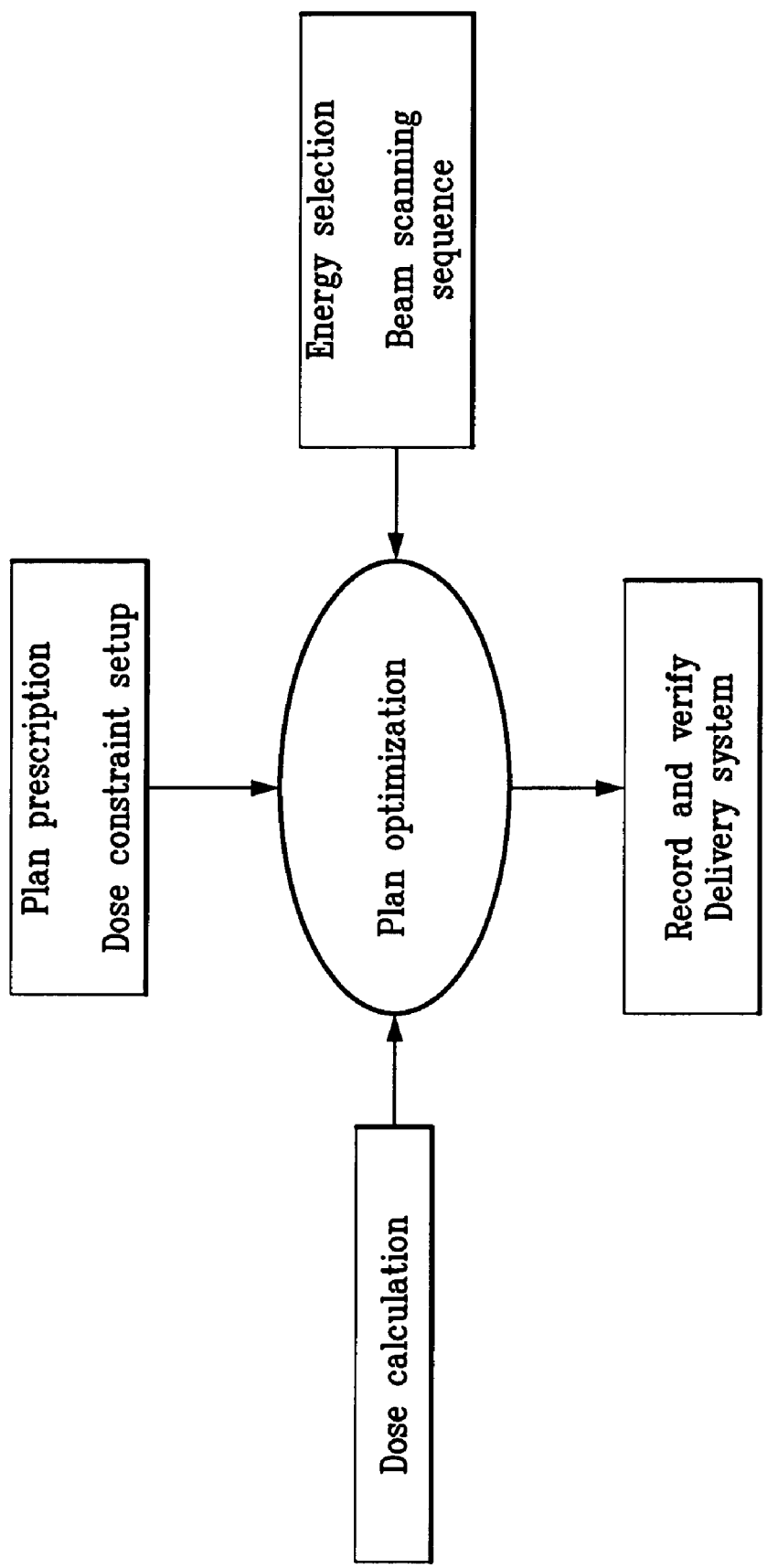
FIG. 1d is a flowchart diagram depicting an overall treatment optimization system of the present invention.

A flowchart for an overall treatment optimization system and method of the present invention is depicted in FIG. 1d. This flowchart shows that the determination of a set of beamlet parameters, e.g., the "plan optimization", is generated based on inputs of a prescribed dose distribution to the target volume and dose constraints for the relevant critical structures, "dose calculation" for individual beamlets/apertures prior to optimization and the final treatment plan post optimization, as well as the choice of available beamlet energy distributions, "energy selection", and beam scanning sequence. The determined set of beamlet parameters ("plan") are recorded, verified and sent to a suitable proton radiation delivery system for providing an optimized prescriptive dose to the targeted volume, as further described herein.

Figure 1E:
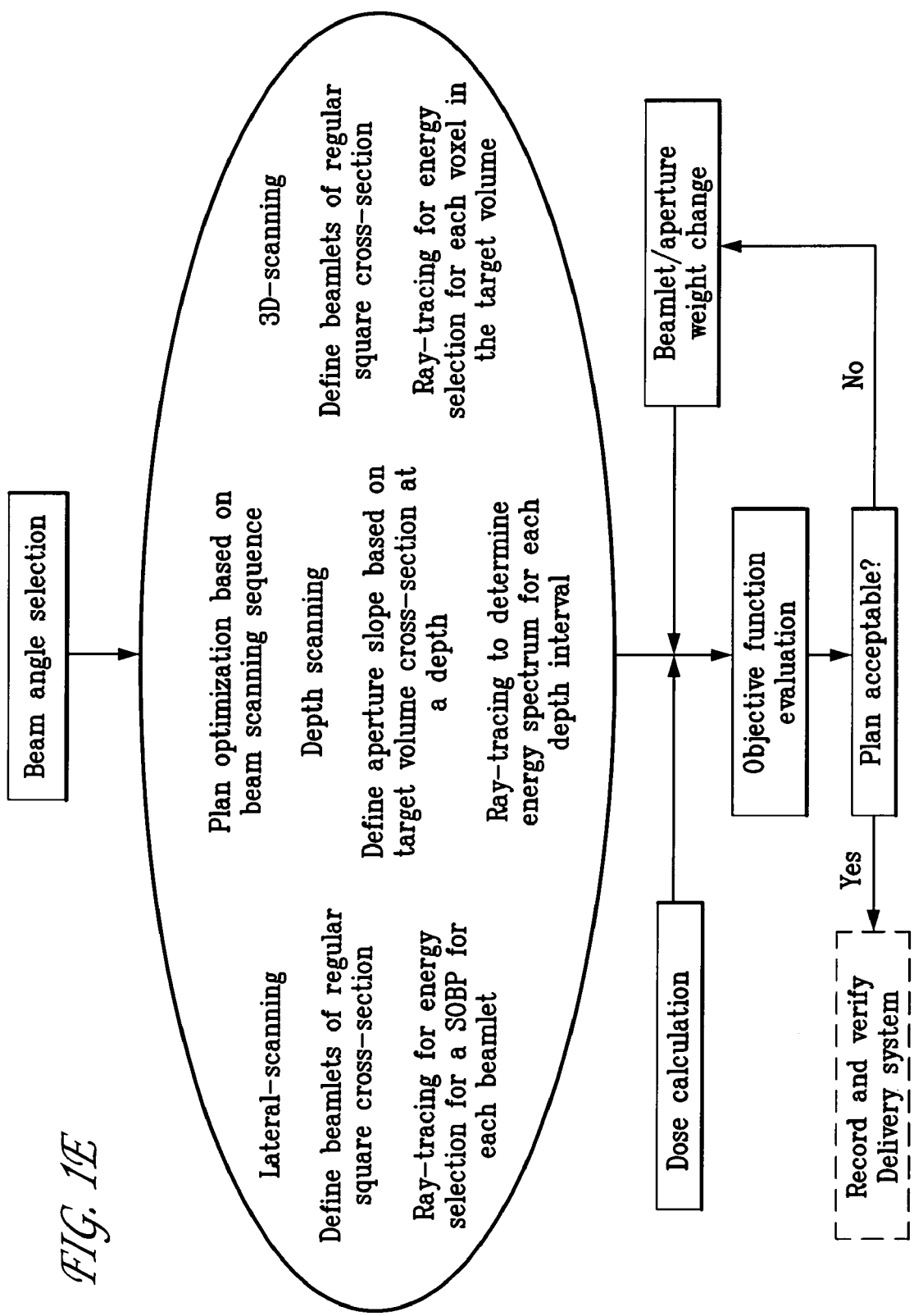
FIG. 1e is a flowchart diagram depicting an overall treatment optimization system of the present invention.
Figure 1F:
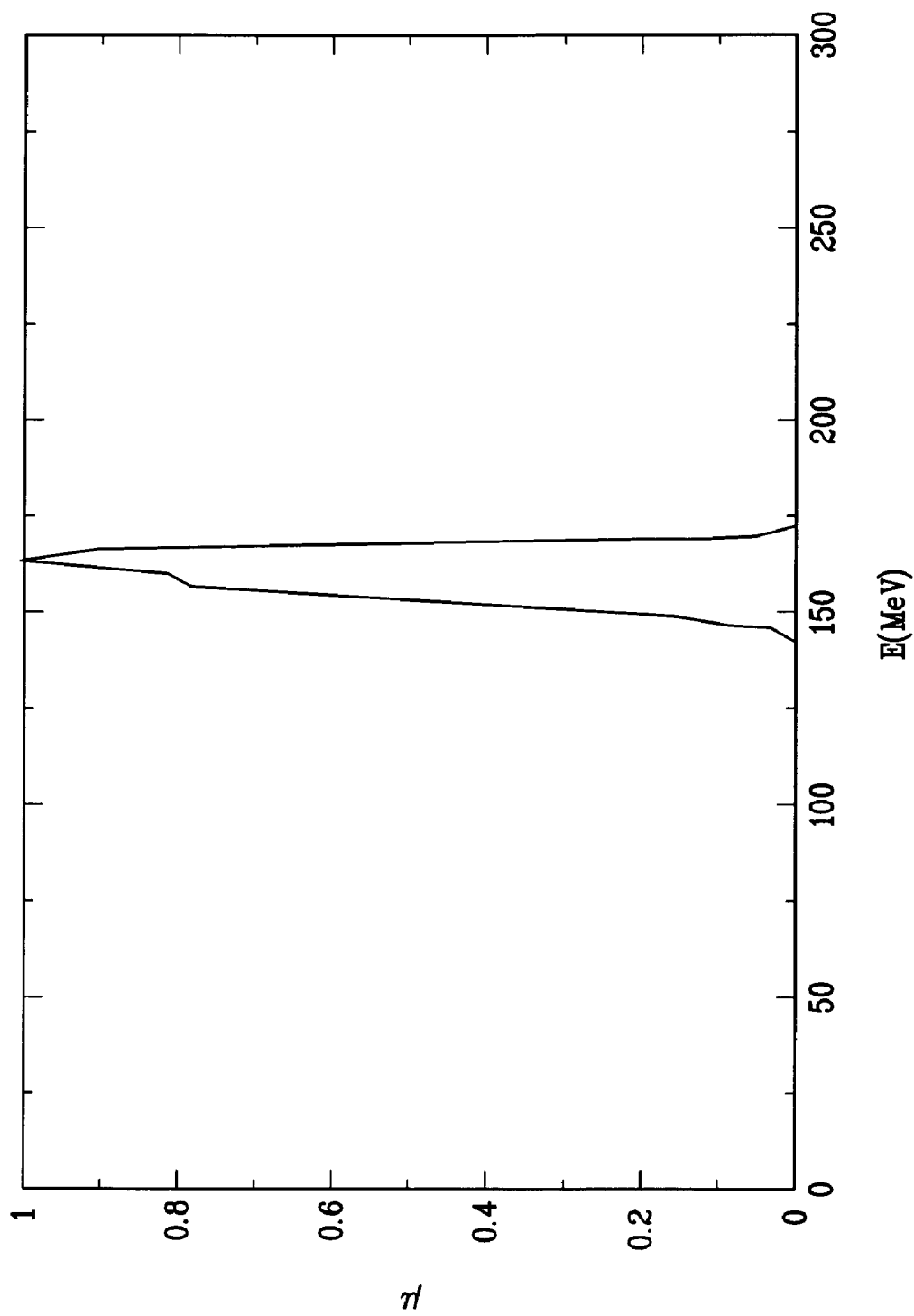
FIG. 1f depicts an example of the proton energy spectrum used in the calculations of the IMPT dose distribution.

An overall treatment optimization system and method of the present invention are also provided in FIG. 1e. Here, the beam angle selection of a plurality of beamlets is provided to the plan optimization method. The beam angle selection can be provided either manually or through a beam-orientation optimization process. The plan optimization method is based on the selection of the beam scanning sequences, which can include lateral scanning, depth scanning and 3D scanning of the beamlets. A lateral scanning beamlet sequence typically divides the whole radiation field that encompasses the beam's eye view cross-section of the target volume into small beamlets of a regular shaped cross-section, such as a square. Each beamlet defines a finite-sized pencil beam. The energy spectrum (i.e., energy distribution) of each beamlet is determined using a ray-tracing algorithm to achieve a desired SOBP along the proton incident direction in the target volume. The entire target volume will be irradiated one beamlet at a time in a lateral scanning manner. Lateral scanning can be conducted by moving the gantry, the patient, or a combination of both. A depth scanning beamlet sequence typically uses one field (or aperture) for a particular depth interval inside the target volume and the aperture shape is determined based on the beam's eye view target volume cross-section at that depth. Multiple apertures may be used for each depth interval to improve target dose conformity and uniformity if needed. The energy spectrum of each aperture is determined using a ray-tracing algorithm to give uniform dose for the corresponding depth interval. A 3D scanning beamlet sequence typically divides the target volume in terms of a plurality of voxels that are individually irradiated (covered) using the Bragg peak of a finite size pencil beam. Each beamlet has a regular cross-sectional shape and area, e.g., a square. The energy of each of the beamlets is determined using a ray-tracing algorithm to ensure the location of its Bragg peak to map or cover a desired voxel of the targeted volume. An objective function, as described further below, is used to compare the plan optimization results to the prescribed dose distribution. The objective function is a mathematical evaluation of the treatment plan based on the prescription dose to the target and the requested critical structure dose constraints. If the plan is acceptable, then the determined set of beamlet parameters ("plan") for the selected beamlet sequence are recorded, verified and sent to a suitable proton radiation delivery system to provide an optimized prescriptive dose to the targeted volume. If the plan is not acceptable, then the beamlet weights are varied (e.g., by modulating the beamlet intensities accordingly based on type of beam scanning sequence selected) until an acceptable plan is obtained.

The examples given below are based on lateral scanning in which the energy is optimized to achieve SOBP for each beamlet and then the intensity of each beamlet is varied, while performing lateral scanning, to achieve 3D dose conformity to the targeted volume. The depth-scanning technique can use an irregular shaped aperture to cover the beam's eye view cross-section of the target volume (or multiple irregular shaped apertures) at a particular depth that is selected using a suitable energy. The target volume can be irradiated using a plurality of variable shaped beamlets that reach varying depths in the targeted volume. The variable shaped beamlets can be provided using a suitable beam collimation system, e.g., a multileaf collimator. Varying depths reached by the beamlets can be provided by varying the energy of the protons using a suitable energy selection system. The depth scanning technique can be used for both laser protons and conventional protons. The depth-scanning technique may be combined with a bolus, range modulator, or both.

In various aspects of the present invention, the optimization methods typically use laser-accelerated protons, although monoenergetic protons (e.g,. generated by conventional synchrotron and cyclotron sources) could also be used. The laser-accelerated protons typically have a small energy spread depending on the beamlet/collimator size in the particle selection/beam collimation device. Accordingly, in certain embodiments of the present invention, the optimization methods can be used in the treatment planning process for both laser-accelerated protons and synchrotron protons. In these embodiments, an integrated hardware/software system capable of delivering beamlets of protons of different incident directions, shapes, sizes, energy spectra and weights is used. Laser-accelerated protons are typically used in the present invention for providing such beamlets of protons.

The energy spectrum for each of the beamlets is typically first optimized to achieve a uniform depth dose distribution and then the intensity of each beamlet is optimized to achieve the overall dose uniformity and conformity to the targeted region. The energy spectrum and intensity of each beamlet are generally different from those of other beamlets, and these characteristics are generally different for different patients. Even for the same patient, they can be different if planned with different targeted region/critical structure dose requirements and optimization parameters. Accordingly, the resulting characteristics of these beamlets will typically be different for different treatment sites, different patients with different dose requirements and optimization parameters/objectives.

In certain embodiments, the energies of the polyenergetic proton beamlets can be modulated, for example, by use of any of the polyenergetic high energy positive ion selection systems that are incorporated by reference herein. Typically, the energies of the polyenergetic proton beamlets are modulated to control the irradiation of the targeted region in the depth direction. Modulation of laser intensity will typically modulate the energy spectrum of the resulting protons emanating from the laser target. More typically, a high energy polyenergetic positive ion selection device is used to modulate the energies of the polyenergetic proton beamlets.

The beamlets can be modulated in a variety of different ways. One way includes the use of a high energy polyenergetic positive ion selection device. Considering that the Bragg peak of a small beam (e.g., a beamlet) of protons is like a "brush" that can be used to "paint" a 3-D target volume, the proton energy is changed to cover the target volume in the beam incident direction (e.g., depth scanning) and scan the beam laterally to cover the target volume at one particular plane (e.g., depth) for lateral scanning. Depth scanning can be performed first for a beamlet and then move to a different beamlet (e.g., location and direction) to cover the 3-D volume. Alternatively, a lateral scanning can be performed first for one plane (e.g., in depth) and then the proton energy is changed to "paint", i.e., irradiate, the next depth. A bolus can be used in combination with this technique to improve dose conformity.

Any number of proton beams can be modulated in various directions, and of various energies and intensities. As used herein, the phrase "modulating a number of proton beams in three dimensions" means to control and deliver proton beamlets with different energy spectra, intensities and incident directions to produce conforming and uniform proton doses in a 3-D target volume. Typically, one proton field (corresponding to an incident direction) is modulated at a time. As described above, depth scanning can be performed first for a beamlet and then move to a different beamlet (location/direction) to cover a 3-D volume. Alternatively, lateral scanning can be performed first for one plane (depth) and then the proton energy is changed to "paint" the next depth, using either regular shaped beamlets or irregular shaped apertures collimated by a multileaf collimator, and/or by use of a bolus.

In certain embodiments, more than one proton source can be used to provide a plurality of beamlets. Multiple sources can be used for reducing beamlet delivery time, and thus time needed for radiation therapy. Each additional source will typically include an integrated laser target, particle selection, beam collimation and dose monitoring system, which is capable of delivering beamlets with different energy spectra, intensities and incident directions.

Suitable polyenergetic proton beams (e.g., beamlets) typically have a range of intensities. The intensity of a proton beam is typically the weight of a beam relative to other beams, which can be related to the fluence of the beam or the dose in a water phantom for this beam (which in turn can be related to the monitor chamber reading if it is used to monitor the fluence or dose). The weight of an open beam is typically assigned the value of 1, and an intensity modulated field typically will have beamlets with intensities varying between 0 and 1. The intensity of each beamlet is suitably modulated using one or more of a variety of available methods. The intensity of a monoenergetic proton beam is typically proportional to the total monitor units ("MU") used to deliver the beam. For a given dose rate, the intensity of a beam is typically proportional to the beam-on time to deliver the beam. The dose rate can also be controlled to change the intensity of a beam for a given beam-on time. For polyenergetic protons generated by laser acceleration, which is a more preferred proton source, each laser pulse typically results in a certain fluence or dose and the intensity of a beam is typically proportional to the number of pulses.

Certain embodiments of the present invention have the ability to select an energy spectrum from a source of polyenergetic high energy protons to deliver a uniform dose in the target volume along the incident direction of the laser-accelerated protons. Energy modulation can be achieved by adding more tissue-like materials (called bolus or modulators) in the proton beams to shift the Bragg peak toward the skin surface. Proton beams of different energies can also be provided that place the Bragg peak at different depths, which is suitably provided using an high energy polyenergetic positive ion beam selection device laser protons. Both depth scanning and lateral scanning of the laser accelerated protons are typically performed to modulate the proton beamlets to provide an optimum dose to a targeted region.

In certain embodiments, both the energy and the intensity of the proton beamlets are modulated during the optimization process. During the optimization process, the weights of individual beamlets are typically varied and the objective function is typically evaluated until a minimum value is obtained which provides an optimal set of weights for the beamlets being optimized. The beamlet weights are optimized based on whether depth scanning or lateral scanning for beam delivery is used.

An optimal dose of polyenergetic proton radiation is typically determined for a particular targeted region in certain embodiments of the present invention. The quality of a treatment plan is typically judged using an objective function, which can be a mathematical evaluation of the treatment plan based on the dose difference between the treatment plan and the prescribed plan, i.e., objective function=$f(D-D_p)$. The plan optimization process typically minimizes the objective function to derive a treatment plan that is closest to the prescribed plan. Accordingly, in certain embodiments, the method modulates the beamlets so that the dose to the targeted region is maximized while the irradiation of critical surrounding structures is minimized, which is typically performed by optimizing the objective function. In other embodiments, the modulating step comprises optimizing the dose to minimize irradiation of critical structures.

In treating different tumors (i.e., treatment targets), different proton dose schemes following different clinical protocols are typically used. Overall doses using polyenergetic high energy protons can typically use the same or similar dosing schemes known for conventional (i.e., synchrotron, monoenergetic) proton beams. Likewise, the threshold (i.e., maximum) radiation that surrounding organs (i.e., critical structures) typically can withstand according to the methods of the present invention will typically vary based on the type of the surrounding organ. For example, the threshold, or tolerance, doses for different organs are well documented, which apply to laser-accelerated polyenergetic protons as well as conventional monoenergetic protons. Accordingly, in certain embodiments the modulating step comprises optimizing the dose to minimize irradiation of organs external to the targeted region.

Various types of software packages suitably can be used to carry out the optimization methods. Suitable software packages typically select optimal beam directions for treating particular tumors. Suitable software typically determines both energy spectra for individual beamlets of optimal beamlet weights (intensities). The software is typically capable of delivering the sequence of these beamlets, for example, to provide the lateral and depth scanning sequences. Accordingly, in certain embodiments the modulating step includes optimizing the dose distribution to achieve the prescription dose to said target. In other embodiments, the modulating step includes optimizing the dose to minimize irradiation of critical structures and optimizing the dose distribution to achieve the prescription dose to said target.

Suitable polyenergetic proton beamlets can be provided by forming a laser-accelerated high energy polyenergetic ion beam including a plurality of high energy polyenergetic protons. Suitable lasers are described in U.S. Pat. No 5,235,606, issued Aug. 10, 1993 to Mourou et al., which is incorporated by reference herein. U.S. patent application Ser. No. 09/757,150, filed by Tajima on Jan. 8, 2001, Pub. No. U.S. 2002/0090194 A1, Pub. Date Jul. 11, 2002, "Laser Driven Ion Accelerator" discloses a system and method of accelerating ions in an accelerator using a high intensity laser, the details of which are incorporated by reference herein in their entirety. Laser-accelerated protons are typically characterized as having a distribution of energy levels. The laser-accelerated proton beam is typically collimated using a collimation device, and spatially separated according to their energy levels using a first magnetic field. The spatially separated high energy polyenergetic protons are subsequently modulated using an aperture, and recombined into a polyenergetic beamlet using a second magnetic field. Related systems, devices, and methods for spatially separating polyenergetic high energy positive ion beams are disclosed in International Patent Application No. PCT/US2004/017081, "High Energy Polyenergetic Ion Selection Systems, Ion Beam Therapy Systems, and Ion Beam Treatment Centers", filed on Jun. 02, 2004, the entirety of which is incorporated by reference herein.

Suitable proton radiation doses are typically provided to the patient as the physical or biologically equivalent dose (or a dose distribution), which can be the dose for one or a few treatments that can be used in radiosurgery type treatments. Suitable proton radiation doses can be provided to the patient for a treatment course consisting of many, such as 20 to 40 fractions, which can be used in radiotherapy treatment of tumors and lesions. Typically, the amount of time needed to provide a dose of proton radiation suitable for radiosurgery or radiotherapy treatment (or a fraction) typically lasts a few minutes or a few hours depending on the total dose, the setup and immobilization device, the beam delivery technique, and the verification method used.

Polyenergetic laser-accelerated protons are selected and delivered in a uniform dose in the target volume along the incident direction of the laser-accelerated protons. Typically, polyenergetic proton beams of different energies are selected using a polyenergetic positive ion beam selection system to place the Bragg peak at different depths in the patient. Tissue-like materials (called bolus or modulators) can also be included in the proton beams to shift the Bragg peak toward the skin surface as necessary.

Any number of laser-provided proton beamlets can be modulated in providing a dose of proton radiation according to the invention. Beamlets may be modulated simultaneously, sequentially, overlapping, or any combination thereof. A patient-specific dose distribution is typically achieved by delivering protons at multiple incident directions, for example, by using different couch- and gantry-angles. Different couch-angles and gantry-angles gives rise to modulation of the beamlet directions. These angles can be varied by rotating the couch, the gantry, or both. A plane of gantry rotation perpendicular to the plane in which the patient lies is called co-planar. Non-co-planar field arrangements can also be used for improving the optimization of the prescribed radiation dose.

Each incident direction is called a field or port, which is divided into sub-fields, which are called beamlets or apertures. These sub-fields may have any shape and size of cross-sectional area, and typically are regular square or rectangular cross-sections in the range of from a few square millimeters ($mm^2$) up to a few square centimeters ($cm^2$) in area. Both regular-shaped and irregular-shaped cross-sections can be used. The dose conformity typically increases with the number of beamlets/apertures used. The delivery complexity and/or delivery time also typically increases with the number of beamlets/apertures used. Depending on the particular treatment design, the beamlet/aperture size and the target volume/shape, the total number of beamlets/apertures typically varies from a few (i.e., about 2 to about 5) to several thousand (i.e., about 2,000 to 4,000), and more likely to be a few tens (i.e., about 20 to 40) to a few hundred (i.e., about 200 to about 400).

The direction (i.e., angle) of each sub-field (beamlet/aperture) is typically determined during the initial selection of the incident beam directions. The protons in each beamlet/aperture will typically have a desired energy spectrum in order to achieve a uniform and conform dose distribution to the targeted region when combined with other beamlets/apertures. The intensity (or weight) of each beamlet/aperture is typically adjusted (i.e., modulated) accordingly to achieve a uniform and conform dose distribution.

Each of the beamlets are typically modulated in at least one dimension, typically, at least two dimensions, and even more typically in three dimensions. Beamlet modulation is typically carried out by rotating and positioning of a suitable gantry that provides the beamlets. In certain embodiments, the intensifies of the polyenergetic proton beamlets can also be modulated in various embodiments of the methods of the present invention. The intensity of the proton beam can be modulated by varying the total proton fluence per laser pulse or by using different numbers of pulses, or a combination of both. The total proton fluence per laser pulse can be controlled, for example, by modulating the laser intensity that reaches the laser target, by changing other laser parameters, by changing the laser target configuration, or by changing the target properties.

In certain embodiments, a targeted region in a patient is irradiated with a desired prescriptive dose of proton radiation. A plurality of modulated polyenergetic proton beamlets is provide and the targeted region is irradiated with the plurality of the polyenergetic proton beamlets. The modulation of the proton beamlets is typically conducted, as described above, to give rise to maximize the dose to the targeted region while minimizing radiation to surrounding tissues.

In another embodiment, three-dimensional intensity modulated proton therapy is provided to a targeted region in a patient. In these methods, a plurality of high energy positive ion beamlets are provided, at least one of the high energy positive ion beamlets is modulated in depth relative to the patient to provide a depth-modulated beamlet, at least one of the depth-modulated beamlets is modulated in a lateral direction relative to the patient to provide a lateral-modulated beamlet, and the targeted region is irradiated with at least one of the lateral-modulated beamlets to the patient. These methods can be carried out with any type of positive ions, for example protons, deuterons, or carbon. These methods can also be carried out with any type of positive ion energy distribution, for example monoenergetic beams as provided by conventional synchrotron and cyclotron sources, as well as polyenergetic positive ions provided by laser-accelerated positive ion sources. Conventional monoenergetic proton facilities can be modified to carry out IMPT by modifying the treatment head to provide beam scanning capability. IMPT using conventional monoenergetic sources provides a 3D technique in which the Bragg peak is scanned through each voxel of the target volume. Scanning the Bragg peak through each voxel can be achieved by moving the patient in one direction (e.g., horizontally), scanning the proton beam in a second direction (e.g., vertically), and varying the proton energy to modulate the Bragg peak in the third direction (e.g., the depth). Conventional monoenergetic protons can be scanned in both lateral directions (horizontal, vertical), for example, by using a rotating gantry. 3D scanning of high energy polyenergetic positive ions, for example laser-accelerated sources, is preferably used, as provided herein. Lateral scanning can be carried out primarily with laser-accelerated protons, and depth scanning method can be carried out using both laser-accelerated protons as well as conventional protons. In this regard, the depth scanning techniques of the present invention enable conventional protons to be used in providing IMPT.

The present invention can be used in the treatment of all types of diseases that are currently treated using conventional external beam radiotherapy/surgery. For example, and number of treatment sites, tumors, or both. All sorts of tumors can be treated, including malignant (i.e., cancerous) as well as benign tumors.

The methods of the present invention can also be extended to heavier high energy polyenergetic positive ions other than protons, for example, deuterons or carbon ions. Accordingly, in certain embodiments the method of providing a positive ion radiation dose comprises the steps of providing a plurality of polyenergetic positive ion beamlets, and modulating the polyenergetic positive ion beamlets, wherein the modulating gives rise to a desired dose distribution (which can be either physical or biologically equivalent dose depending on the treatment design or planning requirements) to a target in both longitudinal and lateral directions relative to the beamlets. The modulating gives rise to a desired prescriptive dose to a targeted region in both longitudinal and lateral directions relative to the beamlets. As protons are a type of positive ions, other positive ions accelerated by laser plasmas will typically have similar characteristics as protons except that they are heavier and therefore require stronger magnetic fields in the particle selection and beam collimation device. Accordingly, the planning and optimizing of treatment dose distributions for high energy polyenergetic positive ions other than protons will typically use the same, or similar, methods as described herein. Typically, polyenergetic positive ions other than protons are provided using any one of a variety of laser targets for providing the positive ions of choice for laser acceleration. Aside from weight and perhaps certain toxicity effects associated with heavier atoms, the methods of optimizing and providing protons as provided herein are also applicable to other positive ions.

EXAMPLES

The examples described below represent a 2.5D modulation/optimization for providing a uniform prescriptive dose of polyenergetic proton beamlets for a prostate tumor. In these examples, the energy is first modulated to achieve the SOBP for each beamlet and then the intensity is optimized of each modulated beamlet to achieve dose conformity (i.e., a uniform prescriptive dose).

Energy modulation calculations. A particle in cell (PIC) (Birdsall, et al., 1985, "Plasma Physics via Computer Simulation", McGraw-Hill Book Company, Singapore) simulation code can be used as previously described (Fourkal et al., 2002) to determine the interaction of a high power laser with a solid high-density foil. Dimensionality of the problem and the importance of nonlinear and kinetic effects make analytical methods typically difficult to provide a detailed description of laser-plasma interactions. The PIC simulation in this case is an effective tool, which can shed light on the complicated problems of laser-plasma interaction. The protons coming out of the thin foil are mainly accelerated in the forward direction by the electrostatic field of charge separation induced by the high intensity laser (Bychenkov, Y. V., et al., "Electron Acceleration by a short Relativistic Laser Pulse at the Front of Solid Targets", *Phys. Rev. Lett.*, 2000, 570-573; Fourkal et al., 2002). Over a period of several tens of plasma frequency cycles, protons are typically accelerated to the relativistic energies reaching maximum value that depends on several factors including the laser pulse length and intensity, and the plasma foil thickness. The late time dynamics, described by the particle in cell simulations shows that the protons reach stationary (not time-dependent) distribution (energy, angular) and move in a formation together with the electrons. This preserves the low proton emittance, shielding proton space charge, which otherwise would provide unreasonably high values for the emittance. The angular distribution of protons exhibits the spread which depends on the energy. The general trend is such that the higher the energy of the accelerated protons, the more they are emitted in the forward direction. The energy spectrum of accelerated protons coming out of the foil resembles a quasithermal distribution, arising from the spatially inhomogeneous electrostatic field structure, which accelerates the protons.

The depth dose distribution calculated using this spectrum shows the high entrance dose and the long tails, which would seem to make it impossible to use laser-accelerated protons in radiation therapy. However, to remedy this deficiency, a particle selection system can be used to reshape the energy spectrum of accelerated protons to yield the SOBP required in proton radiation therapy. Suitable particle selection systems are also described in International Application No. PCT/US2004/017081, "High Energy Polyenergetic Ion Selection Systems, Ion Beam Therapy Systems, and Ion Beam Treatment Centers", filed on Jun. 02, 2004, the entirety of which is incorporated by reference herein. A suitable system disclosed therein is a particle selection device in which a magnetic field is used to spatially separate protons according to their energy and angular distribution. A suitable spatial distribution of the protons is such that the lower energy particles are deflected at greater distances away from the central axis, and as the proton energy increases the spatial deflection decreases. Once such separation is achieved, an aperture is typically used to select protons with a required energy spectrum. Due to a relatively broad angular distribution of the accelerated protons (for a given energy range), there typically will be a spatial mixing of different energy protons once they go through the magnetic field (low-energy protons will go to the regions where the high-energy particles are, and vice versa). To limit this effect, an initial collimation device is introduced, which will collimate protons to the desired angular distribution. As a result of this feature, the spatial mixing of protons typically will always be present (the smaller the initial collimator opening the narrower the spread will be), and in any given spatial location (however small), the proton energy distribution $N_i(E)$ is typically no longer monochromatic, but has a spread around its characteristic energy. The general distribution is such that the protons with lower characteristic energies have a much smaller spread than the protons with higher characteristic energies. Typically, the higher energy protons are not deflected as much in the magnetic field as the lower energy particles. The presence of the energy spread effect modifies the depth dose curves needed for energy modulation calculations. As a result, the depth dose curves will have less sharp fall off beyond the effective Bragg peak as compared to the ideal case of monoenergetic protons. Accordingly, the energy modulation calculations can be modified for each individual beamlet of the given portal. The following procedure is used in the energy modulation calculations (Fourkal, E., et al., "Particle selection for laser-accelerated proton therapy feasibility study", Med. Phys., 2003, 1660-70):

1. The portal of interest is divided into subregions of a given cross section (e.g., 1×1 cm$^2$). A ray tracing program is used to check if the protons belonging to the given beamlet pass through the target. If so, the beamlet coordinate (x, y) and the thickness of the target (z-axis), which is calculated taking into account the density heterogeneities derived form the patient CT data, are recorded.

2. The geometrical size of the target (in the depth direction) determines the proton energy range required to cover it. Using the depth dose distributions for a given energy range, one can compute the weights for each individual polyenergetic beamlet, with the assumption that the weight for the beamlet with the energy distribution, which gives the effective Bragg peak at the distal edge of the target is set to one.

3. Once the weights are known, the proton energy distribution N(E) that will yield a constant physical or biologically equivalent dose along the target's depth dimension (for a given beamlet) can be calculated by convolving the weights $W_i(E)$ with the energy distributions $N_i(E)$ of polyenergetic proton beamlets to give $$N(E) = \sum_i W_i(E)N_i(E) \quad (1)$$

where index i runs through the energies of the polyenergetic proton beamlets needed to cover the area of interest (in depth direction).

4. The above steps are repeated for each individual beamlet with coordinates $(x_i, y_i)$ of all of the portals used in the planning. Once the SOBP energy spectrum for each beamlet is calculated, it is used in the Monte Carlo dose calculations for the given patient geometry.

The energy modulation prescription for protons uses a formulation in which the incident particle differential energy fluence integrated over the surface and solid angle corresponds to the energy distribution defined in Equation (1). The absolute value of each individual weight is correlated to the physical method associated with the actual energy modulation process in the selection system. The actual modulation can be achieved by either using an aperture whose geometric shape is correlated to the weights or by using a slit, which can move along the y-axis in the region where protons are spread according to their energies, and the time spent in a given location will typically be proportional to the value of the weight for the given energy. Convolving the weights with the energy distributions for each individual polyenergetic beamlet according to Equation (1), the actual modulated energy distribution that will deliver the SOBP for the given target's depth dimension and beamlet size is obtained. This energy distribution differs from that calculated using monoenergetic proton beams (for which the weights themselves represent the actual energy distribution) because of the presence of particles with energies beyond those associated with the weights, which is typically a direct consequence of the initial angular distribution of the accelerated protons. FIG. (1f) shows the energy distribution for protons with characteristic energy of 160 MeV and energy spread of 14 MeV at FWHM, calculated using the proposed selection system for an initial aperture opening of 0.6 degrees. The presence of "extra particles" in the distribution will lead to less sharp dose fall off beyond the effective Bragg peak as well as to the reduction of the actual height of the Bragg peak. This introduces some modulation in the calculation of the weights needed for the proton SOBP in Equation (1). In other words, the weights calculated using the polyenergetic protons that the proposed selection system generates are different from those calculated using monoenergetic particles.

Monte Carlo Calculations. Monte Carlo techniques have been employed for both direct and inverse calculations of the dose deposited in a patient by both the proton and photon beams. MCDOSE (Ma, C.-M, et al. "A Monte Carlo dose calculation tool for radiotherapy treatment planning", Phys. Med. Biol., 2002, 1671-89) Monte Carlo code was used to score the dose deposited by the 15 MV photon beam in a 3D patient phantom. To calculate in-patient dose distribution for proton beams a fast and robust simulation algorithm is used (Li, J-S, et al., "Monte Carlo Based Superposition Dose Calculation for Proton Beam Radiotherapy", Med. Phys., 2001, 1250), which is based on the GEANT3 Monte-Carlo simulation tool (Brun, R., 1994, "GEANT3-Detector description and simulation tool Reference Manual"). The anatomy of the GEANT system is such that in-patient calculations using this tool are extremely time consuming making it virtually impossible to calculate the three-dimensional dose distributions in a reasonable amount of time. To remedy this shortcoming, this same algorithm is implemented in the MCDOSE code to calculate the dose deposition in a 3D rectilinear phantom built from patient CT data by superposition of pre-generated Monte Carlo proton tracks. Monoenergetic protons with initial kinetic energy of 250 MeV were simulated in a water phantom using the GEANT3 Monte Carlo code. The changes in position, angle and energy for every step and the energy deposition during this step were recorded for the primary protons and all the secondary particles. When calculating the dose for a particular patient geometry, the pre-generated particle tracks are typically used with the step lengths adjusted based on the density and the stopping power of the local material while keeping the energy deposition unchanged in each step. The tracks are rotated based on the direction of the incident proton, and the scattering angles are adjusted if the phantom materials are different from water. The algorithm is about 13 times faster than GEANT3 for uniform phantom geometry and almost 1000 times faster for heterogeneous phantom geometry. FIG. (2) shows the depth-dose distributions for 80, 150, 250 MeV proton beams in a homogeneous water phantom calculated using both the GEANT3 simulation code as well as the superposition track repeating method. Good agreement (~1%) is observed between both calculation methods.

Optimization Calculations. An optimization procedure based on the steepest descent method (Jiang, S. B., "Development of a compensator based intensity modulated radiation therapy system", *PhD thesis,* 1998, Medical College of Ohio, Toledo, Ohio) was used for the calculation of intensity matrices. The technique is based on the center-of-mass analogy proposed by Spirou, S. V., et al., "A gradient inverse planning algorithm with dose-volume constraints", *Med. Phys.,* 1998, 321-333. In this approach the objective function is a sum of objective functions for the target volume and the healthy tissues as well it includes the target dose-uniformity and critical structure dose-volume/maximum dose constraints to reduce the cold and hot spots in the target volume and critical structures respectively. Thus, the total objective function to be minimized is defined as:

$$F_{obj}(x, r) = f_{obj}^{(tgt)}(x) + f_{obj}^{(hlth)}(x) + P^{(tgt)}(x) + P^{(crit)}(x) \quad (2)$$

$$= \sum_{i=1}^{N^{(tgt)}} (d_i - p_0^{(t)})^2 + w^{(hlth)} \sum_{i=1}^{N^{(hlth)}} d_i^2 +$$

$$r \sum_{k=1}^{2} w_k^{(tgt)} \sum_{i=1}^{N^{(tgt)}} \xi_i (d_i - p_k^{(tgt)})^2 +$$

$$r \sum_{n=1}^{M} w_n^{(crit)} \sum_{k=1}^{L_n} w_{n,k}^{(crit)} \sum_{i=1}^{N_n^{(crit)}} \xi_i (d_i - p_{n,k}^{(crit)})^2$$

where $p_0^{(tgt)}$ is the prescribed dose to the target volume, x is the weight vector, with components representing the weights of each individual beamlet, $d_i$ is the dose given to the point i of the target, $N^{(tgt)}$ is the total number of the dose points assigned to the target, $w^{hlth}$ is the importance weight assigned to the objective function for the healthy tissues, $N^{(hlth)}$ is the total number of dose points assigned to the healthy tissues. The third term in Equation (2) represents the dose uniformity constraints on the target volume. The objective function for the target (first term) has a drawback related to the fact that the underdosing and overdosing are treated equally, which does not reflect clinical observations and considerations, because the cold spots may cause local failure, thus are more important than the hot spots in the target volume. To limit the cold and hot spots in the target volume to an acceptable level a lower- and upper-limit dose-uniformity constraints are applied with the following interpretations "no more than . . . percentage of the target volume should receive a dose lower than $p_1^{(tgt)}$", and "no more than . . . percentage of the target volume should receive a dose higher than $p_2^{(tgt)}$". Parameter $\xi_i$ is the flag defined as 1 when constraint is violated and 0 when it is not, $w_k^{(tgt)}$, k=1,2, is the importance weight assigned to each constraint. The fourth term in Equation (2) represents dose-volume constraints to the critical structures. Its structure is analogous to the dose-volume constraint of the target volume. The optimization problem with various constraints becomes a problem of unconstrained minimization of the objective function (2). The r factor added to the constraint functions will typically be increased as iterations proceed. The minimization procedure is somewhat reminiscent of the calculation of the center-of-mass of the system with known spatial distribution of masses. It stems from the fact that the objective function Equation (2) is minimized when its derivative is equal to zero. The center of mass of the new system is represented by the beamlet weights after one iteration:

$$x^{k+1} = \frac{1}{M} \sum_{i=1}^{N^{(t)}} m_i x_i = x^{(k)} - \frac{1}{M} \nabla F_{obj}(x^{(k)}, r) \quad (3)$$

where the total "mass" is:

$$M = 2 \sum_{i=1}^{N^{(tgt)}} |a_i|^2 + 2w^{(hlth)} \sum_{i=1}^{N^{(hlth)}} |a_i|^2 + \quad (4)$$

$$2r \sum_{k=1}^{2} w_k^{(tgt)} \sum_{i=1}^{N^{(tgt)}} \xi_i |a_i|^2 + 2r \sum_{n=1}^{M} w_n^{(crit)} \sum_{k=1}^{L_n} w_{n,k}^{(crit)} \sum_{i=1}^{N_n^{(crit)}} \xi_i |a_i|^2$$

and a represent the dose-deposition matrix (dose given to the point i from the beamlet j). The algorithm for the center-of-mass method is given as 1. Input the initial values for x and r and convergence tolerance $\epsilon$;
2. Calculate the total mass $M(x^{(k)}, r)$;
3. Calculate the gradient of the objective function;
4. Calculate $x^{(k+1)}$;
5. If $|(F_{obj}(x^{(k+1)}) - F_{obj}(x^{(k)}))/F_{obj}(x^{(k+1)})| < \epsilon$, stop; otherwise r→10* r and go back to step 2.

The overall optimization process can be separated into three stages:

1. Pre-optimization. This stage is the input data for the optimization algorithm consisting of three-dimensional dose calculations in patient's geometry for the initial unitary beamlet weight distribution (each weight is equal to one). The patient's anatomical information (target, critical structures) is stored in a phantom file obtained from the CT data, which is subsequently used by the Monte Carlo simulations to calculate the dose-deposition matrix. This is the stage at which the beam geometrical information is defined including the number of beams, beam margin and orientation, number of beamlets, etc. This is also the stage at which the proton energy spectra (for each beamlet) needed for SOBP are precalculated using Equation (1).

2. Optimization. In this stage, the dose-deposition matrix together with the target dose and various constraints are used as an input for the calculation of the optimal weights of each individual beamlet (intensity profiles).

3. Post-optimization. In this stage, the optimized beamlets weights distribution is used in the final dose calculation and the plan is evaluated using isodose displays and dose-volume histograms.

Results. Two different prostate cases have been studied for the potential use of laser-accelerated protons in intensity-modulated therapy. The basic data consisted of a 80 slice CT study (image matrix per slice 512×512, pixel size 0.95 mm, slice separation 3 mm). The target volume (CTV) as well as four neighboring critical structures were defined (rectum, bladder, left and right femoral heads). Subsequently the CT data set is transformed into the phantom data file for Monte Carlo calculations (image matrix per slice 128×128, pixel size 3.8 mm and slice separation 3 mm). Planning target volume (PTV) was taken to be the CTV with a 5 mm safety margin.

The first plan represents the comparative study between intensity-modulated proton and photon therapy. Both modalities used the same 7-field arrangement as well as the same optimization parameters. Prescription doses for the PTV, dose/volume requirements for the critical structures and the relative importance assigned to all volumes of interest in the optimization procedure are shown in table (1). Analysis of the plans was performed with the help of dose-volume histograms ("DVHs") calculated for each beam modality and volume of interest.

TABLE 1

Prescription/tolerance doses and weights for each volume of interest for the first case study.

| Volume of interest | % of Volume | Prescription/tolerance dose (Gy) | Relative importance |
|---|---|---|---|
| Prostate PTV | 100 | 74.0 | 1.0 |
| Prostate PTV | 5.0 | 72.0 | 1.0 |
| Prostate PTV | 10.0 | 76.0 | 1.0 |
| Rectum | 90.0 | 10.0 | 0.5 |
| Rectum | 50.0 | 20.0 | 0.5 |
| Rectum | 10.0 | 30.0 | 0.5 |
| Bladder | 90.0 | 10.0 | 0.2 |
| Bladder | 50.0 | 20.0 | 0.2 |
| Bladder | 10.0 | 30.0 | 0.2 |
| Femoral heads | 90.0 | 10.0 | 0.2 |
| Femoral heads | 50.0 | 20.0 | 0.2 |
| Femoral heads | 10.0 | 40.0 | 0.2 |

In Table (1) the dose/volume constraints for the target were defined as: "No more than 5% of the target volume should receive a dose lower than 72 Gy, and no more than 10% of the target should receive a dose higher than 76 Gy". All of the target constraints have an importance weight of 1.0. The critical structure constraints were defined as: "No more than 90/50/10% of the rectum/bladder should receive a dose higher than 10/20/30 Gy correspondingly". The rectum has been assigned a larger importance weight to prevent severe complications arising from the overdosing of the rectum.

The second plan represents a comparative study using two-field (parallel-opposed arrangement) and three-field IMPT (parallel-opposed and anterior fields) on one hand, and 7-field photon IMRT on the other as applied to a second prostate case. The optimization parameters used in the calculations are given in Table (2).

TABLE 2

Prescription/tolerance doses and weights for each volume of interest for the second case study.

| Volume of interest | % of Volume | Prescription/tolerance dose (Gy) | Relative importance |
|---|---|---|---|
| Prostate PTV | 100 | 74.0 | 1.0 |
| Prostate PTV | 5.0 | 72.0 | 1.0 |
| Prostate PTV | 10.0 | 76.0 | 1.0 |
| Rectum | 90.0 | 10.0 | 0.1 |
| Rectum | 50.0 | 20.0 | 0.1 |
| Rectum | 10.0 | 30.0 | 0.1 |
| Bladder | 90.0 | 10.0 | 0.05 |
| Bladder | 50.0 | 20.0 | 0.05 |
| Bladder | 10.0 | 30.0 | 0.05 |
| Femoral heads | 90.0 | 10.0 | 0.05 |
| Femoral heads | 50.0 | 20.0 | 0.05 |
| Femoral heads | 10.0 | 40.0 | 0.05 |

The purpose of this study is to explore the dosimetric characteristics of plans (calculated using the physical properties of laser-accelerated protons) with rather small number of fields and to show that fewer field arrangement for laser-accelerated protons can still yield both a superior dose distribution within the target and significant sparing of the surrounding healthy tissues. This signifies the possibility of using a limited number of ports to generate clinically acceptable plans, which would lead to a significant reduction of treatment time without compromising the dosimetric requirements on the target and critical structures. The small number of fields can inherently lead to a better sparing of critical structures, since the given field arrangement can simply avoid some critical structures (e.g., parallel-opposed beam arrangement for prostate cases avoids the rectum and the bladder, but goes through the femoral heads), thus minimizing the dose deposited in them, but on the other hand the target dose homogeneity is somewhat compromised in intensity modulated radiation therapy using photons with a smaller number of fields. In other words, in order to achieve both a desired prescriptive target dose distribution and desirable sparing of the healthy tissues, one needs to use rather large number of fields (six or more) in photon IMRT, but can achieve a superior dose distribution using fewer fields with IMPT. Energy modulation of protons that allows for a precise dose conformity (geometric as well as dosimetric) along the target's depth dimension is very difficult, if not impossible, to achieve with photons.

Target coverage, critical structure doses and normal tissue integral dose. FIGS. (3) and (4) show isodose distributions for both cases considered here. The increased normal tissue dose load for photon beam modality is clearly observed in these figures as is the excellent dose conformation to the target volume for the proton beam modality. Comparative DVHs for the PTV, rectum, bladder and both femoral heads are shown in FIGS. (5) to (7). The Dose volume histograms for both plans were normalized so that 95% of the PTV's volume received 74 Gy (prescription dose). The two and three field arrangement for protons (case 2) show almost identical target dose coverage with 4.5% dose inhomogeneity, defined as $$\eta = \frac{D_5 - D_{95}}{D_{95}}.$$

At the same time the 7 field photon IMRT (case 2) exhibits 9% dose inhomogeneity. The seven field proton and photon examples (case 1) exhibit 9.5% and 14.5% of dose inhomogeneity respectively. Comparative DVHs for the rectum, bladder and both femoral heads show a superior sparing of these organs for intermediate dose levels using proton modality (for all field arrangements studied). At approximately 45 Gy dose level however, IM photon curve crosses the IMPT, indicating little difference in sparing effects between IMPT and IMRT at high dose levels. This peculiarity in the dose distribution has its origin in the definition of the PTV, which usually encroaches into the critical structure domain (see discussions in the next section). The critical structure DVHs for plan 2 show almost 50/30% volume reduction of the bladder/rectum irradiated to 15 Gy dose level using a small but selective beam arrangement (parallel-opposed for prostate) for proton modality over that with the three-field technique, stemming from the geometric missing of the rectum/bladder for this field arrangement. The femoral head DVHs for case 2 show somewhat better sparing of these structures by the three-field technique as compared to the parallel-opposed arrangement.

The mean (integral) dose to the normal tissues (tissue other than target and critical structures) and critical structures is an important issue in radiation therapy since it is related to the normal tissue complication probability as well as to the possibility of induction of secondary malignancies. The use of particle modalities (protons, other heavy ions) with a superior depth dose characteristics to that of photons remains the only way to reduce the normal tissue dose even when compared to state of the art optimization techniques (Lomax 1999c). In Tables (3)-(5), the mean doses to the non target normal tissues and critical structures for both IM particle modalities are shown. Both the normal tissue and critical structure mean doses are higher for photon beams.

TABLE 3

Mean dose to all normal tissues (Gy) for different particle modalities.

| Particle modality | Case 1 | Case 2 |
|---|---|---|
| Photons | 8.96 | 5.06 |
| Protons | 3.42 | 2.29 |

TABLE 4

Mean dose to the rectum (Gy) for different particle modalities.

| Particle modality | Case 1 | Case 2 |
|---|---|---|
| Photons | 27.52 | 28.68 |
| Protons | 15.17 | 10.64 (2field) |
|  |  | 12.89 (3field) |

TABLE 5

Mean dose to the bladder (Gy) for different particle modalities.

| Particle modality | Case 1 | Case 2 |
|---|---|---|
| Photons | 22.79 | 33.46 |
| Protons | 8.4 | 16.3 (2field) |
|  |  | 23.54 (3field) |

Laser-accelerated IMPT versus the "ideal" case of IMPT using monoenergetic protons. A 7-field arrangement (case 1) described earlier was used to do the comparative study between the laser-accelerated IMPT and the ideal case of IMPT using monoenergetic protons. The prescription dose for the PTV, dose/volume requirements for the critical structures and relative importance assigned to all volumes of interest in the optimization procedure are the same as used in the proton-photon 7-field comparative study and are shown in table (1). Comparative isodose line distributions and DVHs for the PTV, rectum, bladder and both femoral heads are shown in FIGS. (8-10). As in previous cases the DVHs were normalized so that 95% of the PTVs volume received 74 Gy. FIG. (8) shows that the isodose line distribution for the ideal case of monoenergetic protons exhibits somewhat higher dose gradients (line compression) than that for IMPT based on laser-accelerated protons. At the same time, both IMPT modalities yielded almost identical PTV dose coverage with 12% dose inhomogeneity for the monoenergetic case and 14.5% dose inhomogeneity for laser-accelerated IMPT. All of the critical structure DVHs exhibit slightly better dose distributions for the monoenergetic case consistent with the isodose line pattern.

Discussion of Results. The results of treatment planning comparisons between IM proton (laser-accelerated) and IM photon modalities as well as a comparison between laser-accelerated IMPT and the ideal case of IMPT using monoenergetic protons have been presented above. These results show the utility of laser-accelerated protons for intensity modulated radiation therapy. These results also provide quantitative information about the dosimetric advantages of the disclosed methods. The comparative study between both proton modalities plays an additional role in relating the dosimetric characteristics of laser-accelerator-based technology to those that use conventional proton acceleration methods. From comparing the isodose line distribution and DVHs for the PTV and organs at risk, slightly better dose distributions in critical structures for the ideal case of IMPT is observed. Intensity modulated therapy based on monoenergetic protons corresponds to a best case scenario that should give the best possible dose distributions. The fact that laser-accelerator-based IMPT plans can generate dose distributions that are comparable to those using the monoenergetic protons is indeed quite surprising.

From the proton-photon case studies, it can be concluded that the IM proton plans provided a better coverage of the targeted region than the IM photon technique. In addition, the proton beam modality yielded significant reduction of mean doses to critical structures and normal tissues as seen from Tables 3-5. The volumes of critical structures irradiated to the intermediate dose levels ($D \leq 45$ Gy) was significantly lower for proton modality. At 45 Gy dose level however, little difference was seen between the volumes of critical structures irradiated by the IM photon or IM proton plans. The reduction of the critical structure mean doses for both forward and inverse proton planning is attributed to the physical advantages of the protons, even though different methods (inverse versus forward) have been applied in both studies. For some critical structures it is important to conform the dose to the prescribed tolerance level to reduce the possibility of complications. But at the same time the importance of high dose sparing in comparison to reduction of intermediate doses depends on the volume effect displayed by all critical structures. For serial organs, the importance of reduction of the volume irradiated to high dose levels typically overweighs that of reduction of the volume irradiated to median dose levels. For parallel organs (e.g., lungs) on the other hand it is typically more important to reduce the mean dose to these structures (or reduce the volume irradiated to medium dose levels) rather than the reduction of the high dose volume. An important example signifying the confusion concerning the issue of the volume effects is the rectum case. It was generally believed that the rectum was a serial organ (Burman, C., et al. "Fitting of normal tissue data to an analytical function", *Int. J Radiat. Oncol. Biol. Phys.*, 1991, 123-136; Emami, B., et al., "Tolerance of normal tissue to therapeutic irradiation, *Int. J. Radiat. Oncol. Biol. Phys.*, 1991,109-122), but in recent study it has been suggested to be a parallel organ similar in response to lungs (Nahum, A., "The potential of normal-tissue radiobiology for the physics of conformal therapy", *Tissue effects in radiotherapy: physics meets biology*, Betchworth UK, 1997). Therefore, without a more accurate knowledge of the volume effect in critical structures, it is difficult to judge the relative importance of critical structure DVHs. As a result of this uncertainty it is desirable to reduce the medium as well as the high doses in all critical structures. As shown herein, this can be better achieved through the utilization of optimization techniques for proton beams than through the use of IM photons.

As mentioned earlier, one aspect of the present invention is to provide the dosimetric characteristics of radiation therapy plans computed through the use of the physical properties of laser-accelerated protons that are coming out of the selection system. The dosimetric characteristics of the computed plans are typically functions of the intrinsic physical properties of particle beams (e.g., energy spectrum, angular distribution) that depend on the methods of producing the clinically acceptable beams (e.g., spot scanning versus passive scattering for conventional proton beams). The laser-accelerated protons coming out of the particle selection system typically have some energy spread, which leads to a less sharp fall off of the dose beyond the Bragg peak. Without being bound by a particular theory of operation, it is believed that this introduces some modulation to the final in-phantom dose distribution pertaining to the parameters of this particular acceleration and selection method.

Both cases considered above yielded a superior target dose coverage and sparing of the critical structures for proton beams. The target coverage in the first case study revealed a somewhat better dose homogeneity achieved by the proton beams with the large number of fields (7 field arrangement) over the same field arrangement for photons. The following angles were used in a 7-field arrangement calculation: 90, 45, 0, 315, 295, 260, and 215 degrees in the plane of gantry rotation that is perpendicular to the plane in which the patient lies. The results of the case study 2 where the dose homogeneity for 2 proton field arrangement indicates that the smaller number of fields can lead to a better coverage of the target for proton modality. This is somewhat counterintuitive to conventional understanding of IM techniques in which an excellent target coverage can be achieved through the use of the larger number of fields. To understand this, and without being bound by any particular theory of operations, the meaning of the three dimensional intensity modulation as applied to laser-accelerated protons is further elucidated. Proton therapy can be viewed as an intensity modulated form of radiotherapy emanating from the possibility of modulation of the initial proton energy spectrum to achieve SOBP. In conventional proton therapy, range shifters are used to obtain SOBP. The high energy polyenergetic positive ion selection system that can be used with laser-accelerated protons achieves the same task by using a magnetic field to rebuild the initial proton energy spectrum. In the three dimensional intensity modulation prescription, the given port is subdivided into small areas (beamlets). Protons belonging to different beamlets traverse different parts of the targeted region with various targeted region thicknesses leading to different energy spectra required to give SOBP. In other words, the particle selection system will produce beamlets with different energy spectra correlated to the corresponding targeted region thicknesses. Depth dose distributions calculated using these spectra exhibit a correlation between the energy distribution and the height of the individual beamlet's SOBP. The deeper the distal part of the targeted region is the lower the absolute value of the SOBP will be. This typically stems from the higher the proton energy, the lower the absolute height of an individual Bragg peak (see FIG. (2)). As an example, FIG. (11a) shows different spread out Bragg peaks calculated using corresponding proton energy spectra shown in FIG. (11b). These energy distributions (obtained originally from the solution to the Equation of motion for protons in the magnetic field with initial conditions provided by the PIC simulations) were calculated for individual beamlets in the IM calculations and reflect the internal energy spread inherent to the selection system proposed earlier. The absolute height of each individual SOBP is different, which would eventually lead to an undesirable dose distribution within the targeted region. If there were no critical structures present, the optimization procedure could easily find such distribution of beamlet weights that would lead to highly desired prescriptive dose within the targeted region (the optimized weight distribution would be such that the height of each individual beamlet's SOBP would be the same). Table (6) shows the weight distribution for beamlets with energy spectrum shown in FIG. (11(b)) that provides a desired prescriptive dose. The weights were obtained by simple normalization of each individual SOBP to that corresponding to the coverage of the most deeply located portion of the targeted region.

TABLE 6

Beamlet weights distribution needed to obtain a desired prescriptive dose

| Distribution | Weight |
|---|---|
| 1 | 1.0 |
| 2 | 0.88 |
| 3 | 0.68 |
| 4 | 0.56 |

The presence of critical structures typically will introduce some modulation into the final beamlet weight distribution (to limit the dose in the critical structures), so that the targeted region dose becomes less homogeneous. Without being bound by any particular theory of operation, this appears to be why the 2-3 proton field arrangement in case study 2, yielded a better target dose coverage. The two field arrangement (parallel-opposed) for a second prostate case spares the rectum and the bladder, but goes directly through the right and the left femoral heads. As a result of this field arrangement, the number of beamlets that go through the rectum and the bladder are small leading to relatively easy satisfaction of constraints on these critical structures and the targeted region in the optimization procedure.

Figure 7:
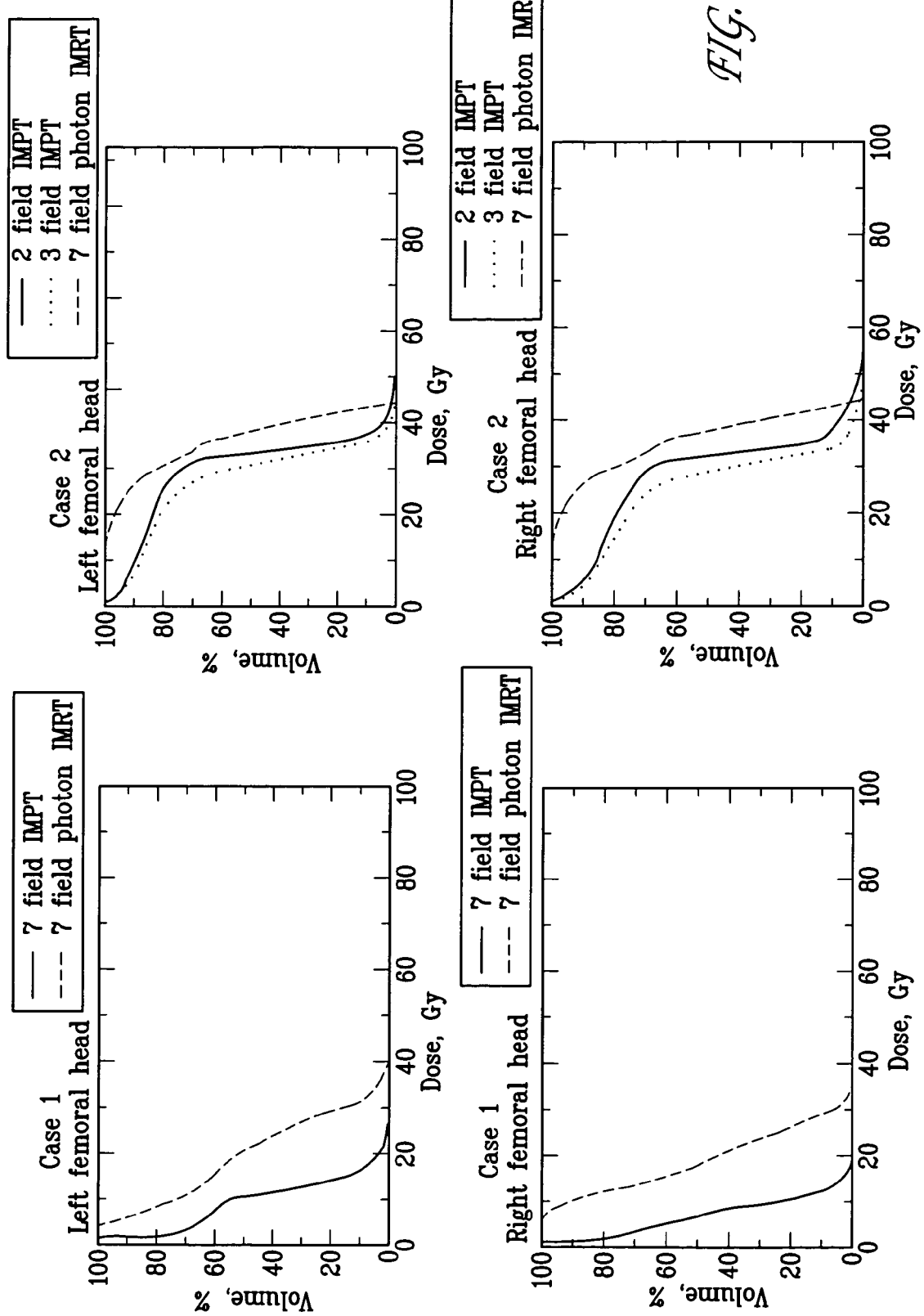
FIG. 7 provides dose-volume histograms for the left and right femoral heads. The plans were normalized to 95% of the PTV's volume, which receives 100% of the prescription dose of 74 Gy.
Figure 8:
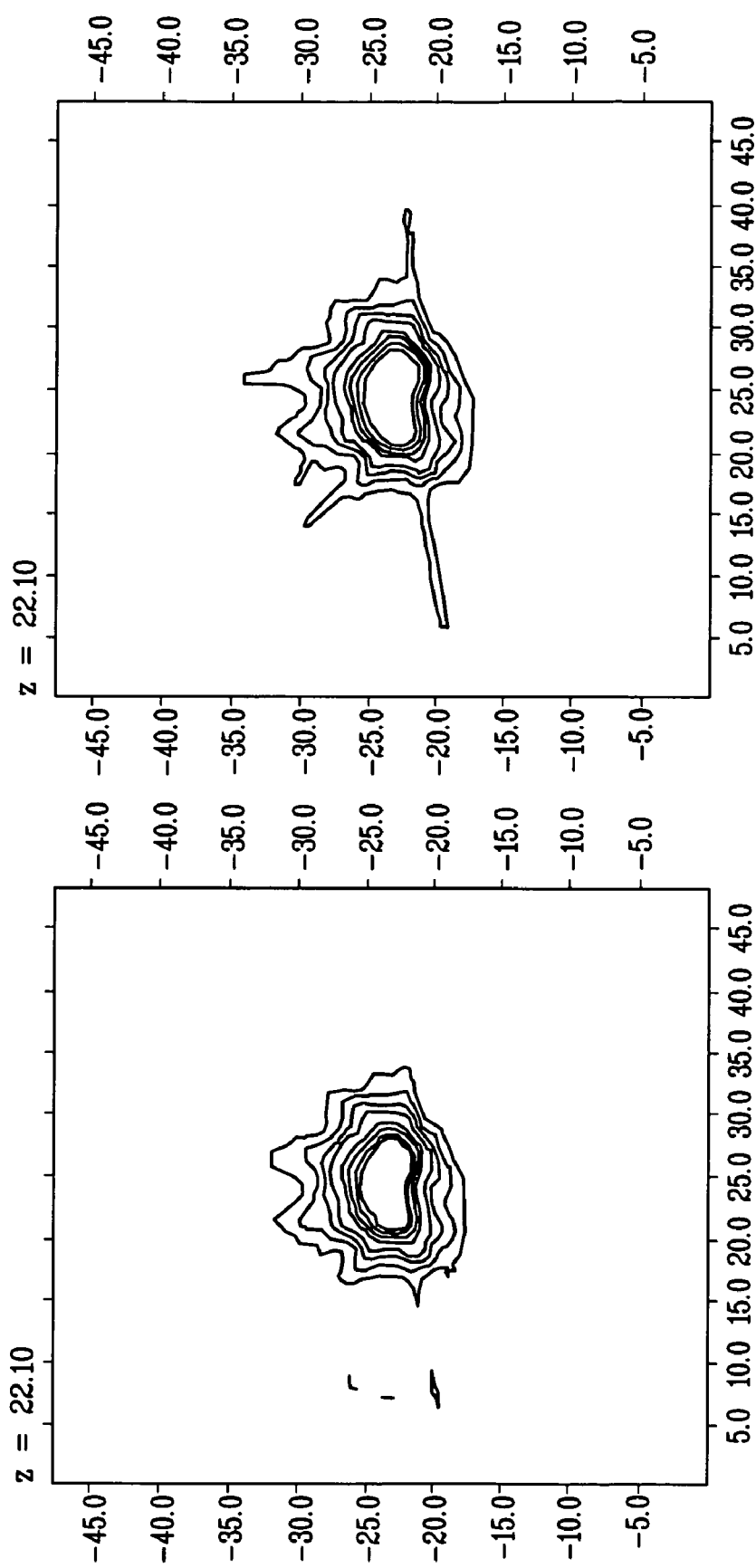
FIG. 8 provides isodose line distributions (case study 1) for comparative proton IMPT for (A) 7 field IMPT using monoenergetic protons and (B) 7 field IMPT using laser-accelerated protons. The outermost line represents 20% of the prescription dose. The innermost line represents 100% of the prescription dose. The prescription dose is 74 Gy to 95% of the target's planning volume. The isodose distributions of 10% of the prescription dose and lower are not shown.
Figure 9:
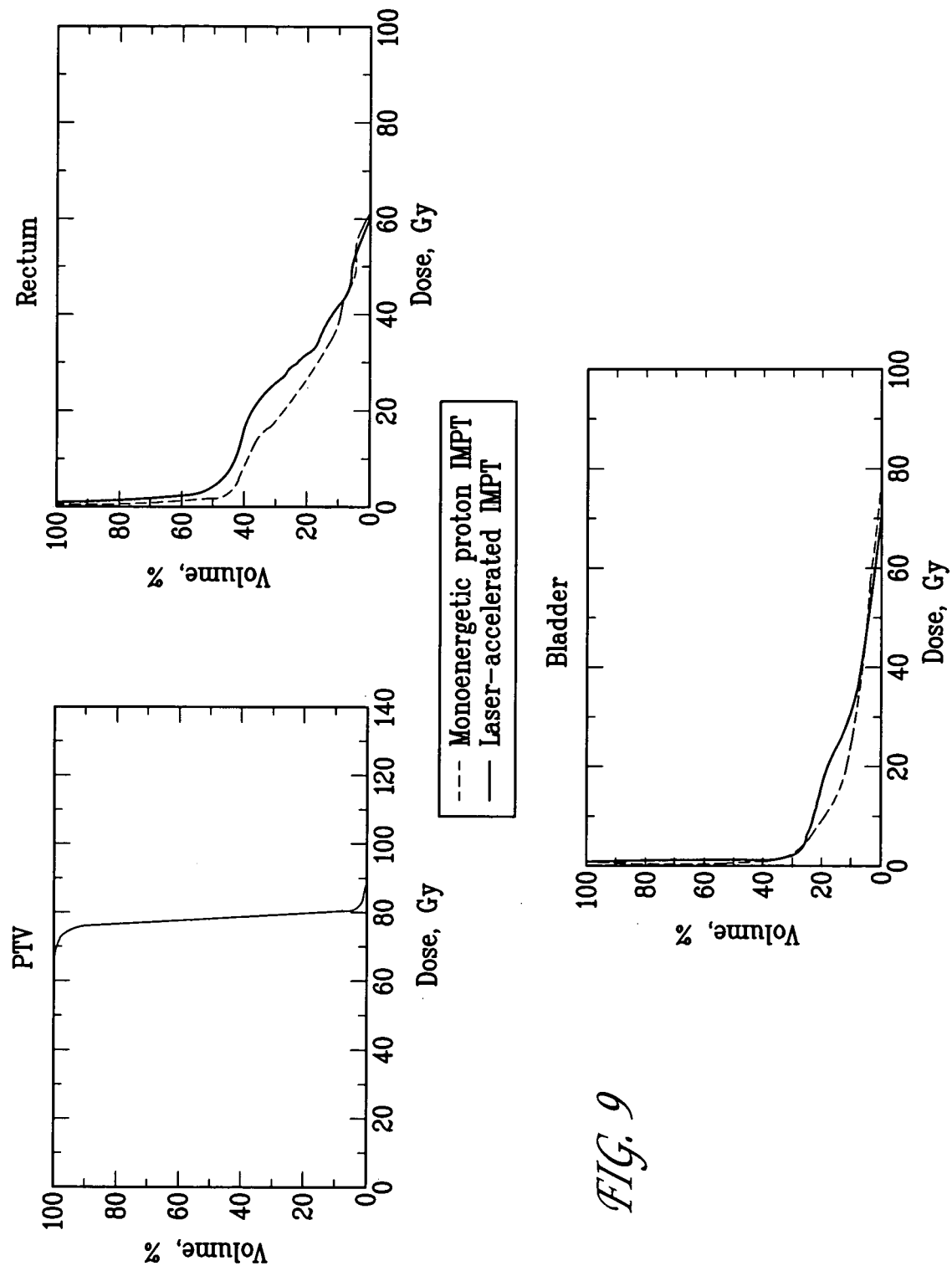
FIG. 9 provides dose-volume histograms for the PTV, rectum and bladder. The plan was normalized to 95% of the PTV's volume, which receives 100% of the prescription dose of 74 Gy.
Figure 11A:
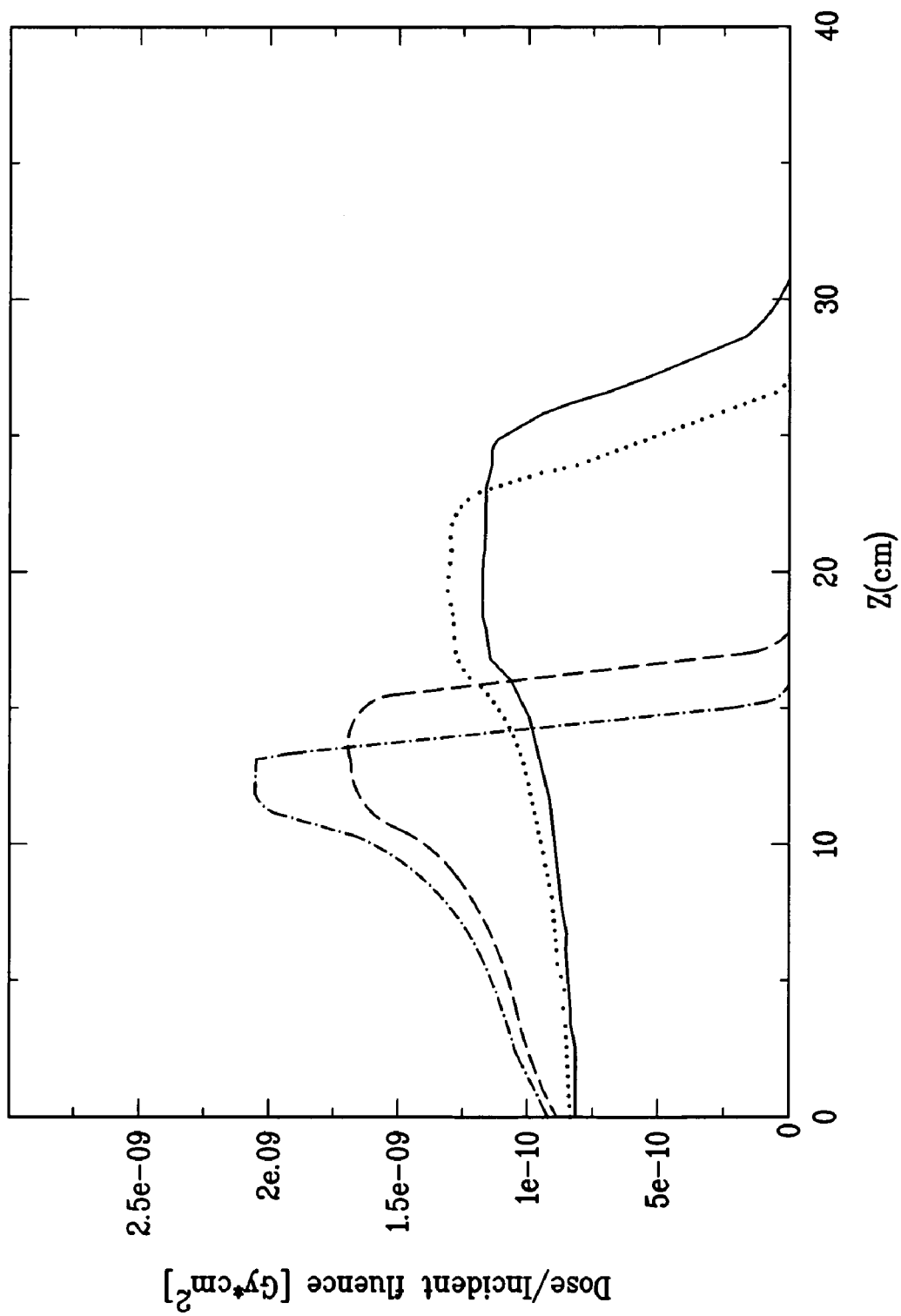
FIG. 11 provides (a) central axis depth dose distributions of the SOBP obtained using different energy spectrum; and (b) the proton energy spectra needed to obtain the SOBPs.
Figure 11B:
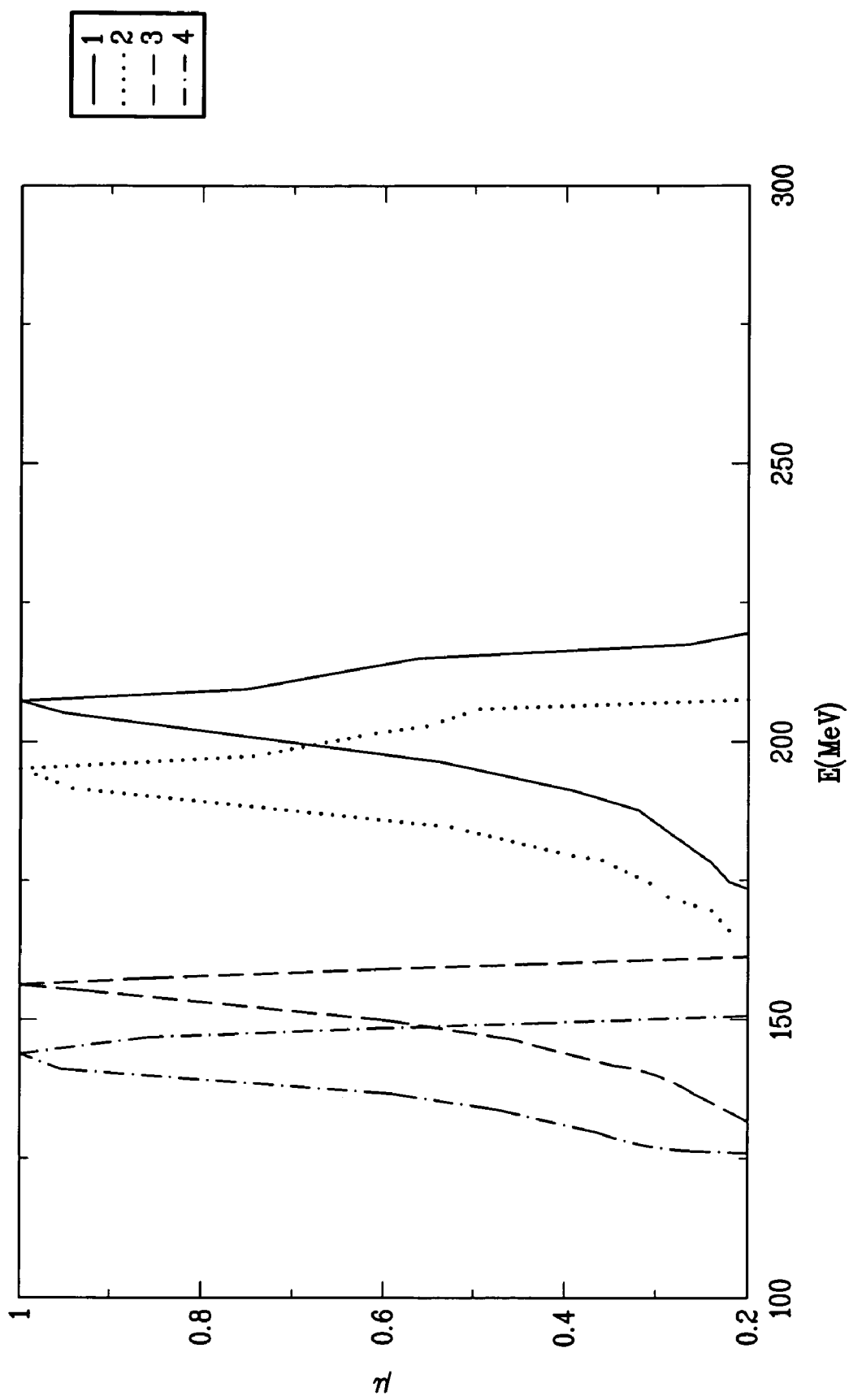

From FIG. 7 one can see that the parallel-opposed beam arrangement (case study 2) exhibits relatively high dose deposited to both femoral heads. The tolerance dose to these structures adopted at Fox Chase Cancer Center, Philadelphia, Pa., is such that no more than 10% of their volume can receive the dose of 50 Gy or higher (for target prescription of 74 Gy and prescription regiment of 2 Gy/fraction). The femoral head DVHs for case 2 show that only 0.28% of the left femoral head and 1.4% of the right are receiving the dose higher than 50 Gy, which is well within the tolerance level. These results lead to one conclusion that intensity modulated protons can and should provide excellent radiation therapy plans with a small number of fields. The exact number of fields needed to generate an acceptable plan depends on the target volume, its shape and location (relative to critical structures), but with a wise choice of angles for incoming fields (dictated by the geometric avoidance of the critical structures), this can be accomplished.

The implementation of intensity optimization (in the direction perpendicular to the proton beam propagation) techniques for proton therapy can also be provided by using an "intelligent" set of ports, proton beams can deliver superb dose distribution without resorting to the time consuming optimization procedures. Each individual beamlet's weight can be calculated using the absolute height of the SOBP to yield an extremely desired prescriptive dose in the targeted region as well as to minimize the dose in the critical structures (through the wise choice of port angles).

An interesting issue related to both cases is the volumes of the critical structures irradiated to high doses. From FIG. (6) the volumes of the rectum and the bladder irradiated to the doses of 45 Gy and higher for proton and photon intensity modulated plans are almost the same. Without being bound by a particular theory of operation, the reason behind this similarity seems to be that the PTV overlaps with parts of the rectum/bladder that are adjacent to the posterior/anterior portion of the targeted region. The optimization conditions used for both cases, required the highest priority for conforming the dose to the PTV, so that those parts of the bladder/rectum that overlap with the PTV receive prescription dose, which is seemingly independent of the particle modality. This leads to a correlation between the DVHs for critical structures and those for the targeted region. The reduction of the volumes of the critical structures irradiated to high doses will tend to reduce the dose to some portion of the targeted region making the target dose distribution more inhomogeneous. A highly homogeneous dose (i.e., a highly desired prescriptive dose) in the targeted region on the other hand is achieved at the expense of the increased dose to the critical structures. This feature will typically be present as long as there exists an overlapping between the critical structures and the target volume.

As shown in table (3), the integral dose to the normal tissue is greatly reduced for proton beams as compared to that for the photons (an average reduction of almost three times). The clinical importance of low doses to large volumes remains to be investigated, but there are cases where the reduction of the normal tissue dose may play a significant role (pediatric cases, treatments of recurrences, radiotherapy in conjunction with chemotherapy or surgery).

The present invention provides methods of providing therapeutic doses of laser-accelerated proton radiation, in particular laser-accelerated protons for intensity modulated radiation therapy. The particle selection systems previously described in PCT/US2004/017081 are capable of producing clinically relevant proton beams that can be used in conjunction with the optimization techniques described herein to produce excellent radiation therapy treatments. Monte Carlo based treatment planning software together with steepest descent optimization algorithm were used to calculate dose distributions for two prostate cases. It was found that the use of laser-accelerated protons could greatly improve the target dose homogeneity and reduce mean and intermediate dose to critical structures when compared to intensity modulated photon treatments. Proton and photon intensity modulated techniques delivered similar doses to the critical structure volumes enclosed in the PTV. Also, clinically acceptable plans can be generated with a small number of fields (2-3 per treatment) for intensity modulated therapy using laser-accelerated protons.

Results indicate that laser-accelerated protons can be modulated using the methods described herein to provide superior clinical radiation therapy treatments that will significantly improve the management of cancer. Extension of these methods to a variety of tumors and lesions is well within the purview of those skilled in the art with the benefit of the present disclosure.

Example of a System Design. A suitable laser-proton therapy system and results of a feasibility study on energy- and intensity-modulated radiation therapy using laser-accelerated proton beams is provided in this section.

The massive cost of prior art particle therapy facilities arises from expensive particle accelerator but also because of the associated costs for the gantries, the beam lines, the switchyard, and the shielding required, which represent 50-70% of the overall cost. Therefore, a less expensive particle source may not solve the problem if one still has to transport the particle beams through long beamlines to different treatment rooms/gantries. Also, laser-accelerated protons have a broad energy spectrum, which produce a clinically unfavorable dose distribution and cannot be transported using conventional beamlines that are designed for monoenergetic protons. A solution to this problem is to transport the laser beam to each of the treatment rooms and to design a compact gantry to include the target assembly, the particle/energy selection, the beam collimation and monitoring system so that we can retrofit it in a conventional linac room. This can reduce cost by at least an order of magnitude relative to that for a conventional (prior art) proton therapy facility.

FIG. 1A shows a schematic diagram of a laser proton therapy unit. The laser is transported directly to the gantry (not shown). The target assembly and the beam selection device can be placed on the rotating gantry (not drawn), and the laser beam can reach the final focusing mirror (f) through a series of mirrors (a-e). The distances between mirrors (d) and (e) and mirrors (e) and (f) can be adjusted to scan the proton beam along the x and y axis, respectively, which can generate a parallel scanned beam. An alternative method is to swing the target and beam selection device about the laser beam axis defined by mirrors (d) and (e) and that defined by (e) and (f), respectively, to achieve a scan pattern. This can generate a divergent scan beam. The treatment couch can be adjusted to allow for multiple beam arrangement with coplanar and noncoplanar, and isocentric and SSD (source-to-surface distance) treatments.

Figure 12:
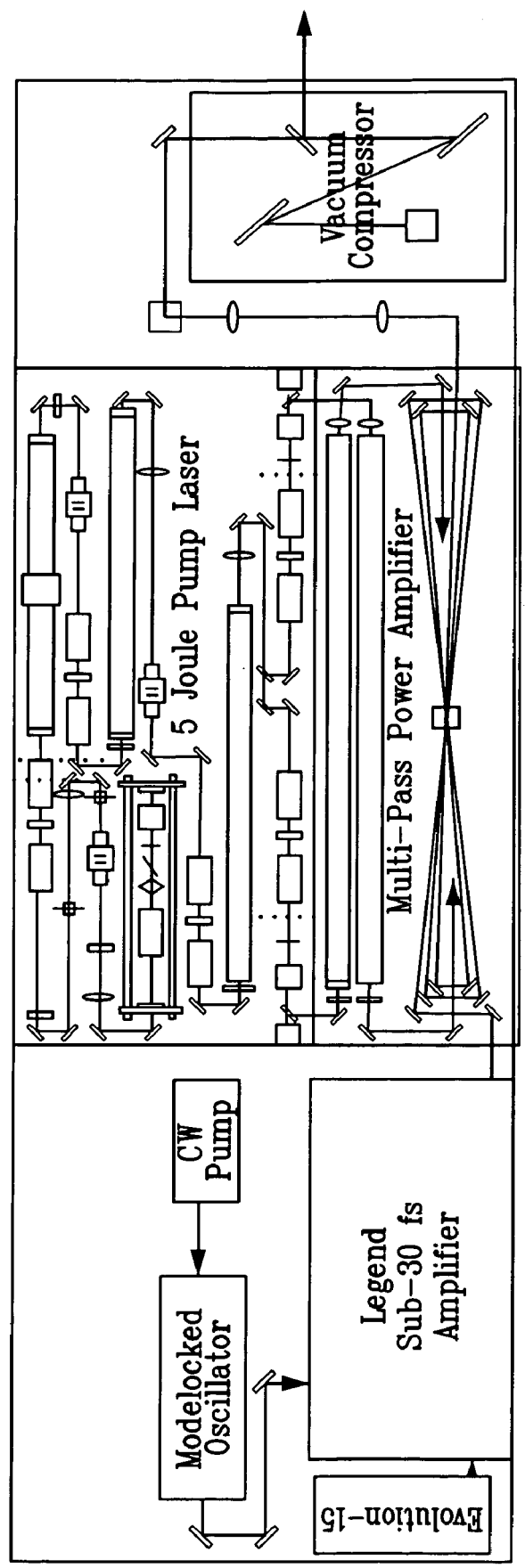
FIG. 12 is a schematic diagram of the high-power laser system used for this project.

Laser system. A suitable laser system for a laser-proton therapy system can be based on commercial femtosecond oscillator and multiple stages of amplification (see FIG. 12). The first component is a conventional modelocked Mira Ti:sapphire oscillator pumped by a 5-watt CW Verdi laser at 532 nm. This setup generates a stream of 20-femtosecond pulses at a repetition rate of 80 MHz. This output then feeds into a Legend regenerative amplifier, operating at 1 kHz, pumped by a 10-watt Q-switched Evolution laser at 527 nm. The output is then pulse-picked and fed into a 10-Hz TW multipass amplifier. The TW amplifier is pumped by the 4.0 J/pulse output of a custom-built TEMOO Nd:YAG laser and delivers output pulses with energy >1 J. Finally, the 800-nm output is stepped up to 5-15 J/pulse levels in a second stage multipass amplifier, which is pumped by the 50 J/pulse frequency-doubled output of an Nd: glass laser. Most pump lasers for Ti : sapphire amplifiers are frequency-doubled Nd : YAG, and Nd; YLF but Nd: glass can store much higher energy and is therefore preferred for reaching the highest possible Q-switched green pump energies required for this research. The low thermal conductivity of Nd : glass limits this powerful pump laser to about I pulse/4 minutes. Higher thermal conductivity amplifiers and better heat transfer should help increase the pulse rate. After leaving the Nd: glass pumped amplifier, the output pulses are compressed to between 40 and 50 fs in a custom-made vacuum pulse compressor, which incorporates large diameter gratings in order to handle the high pulse energy. The pulse compressor is enclosed in a vacuum because at these energy levels the laser pulses would cause breakdown in air as it propagates.

Target. A suitable target assembly can include a final focusing system and a target holder. The target assembly is contained in a vacuum chamber inside the treatment gantry together with the particle selection beam collimation system. Particle-in-cell (PIC) simulations have been made to study optimal laser parameters and target geometries. Different laser parameters and target configurations have been simulated. The results of PIC simulations have been used to derive particle phase space data for dose calculation and treatment optimization studies. Bi-layer targets are primary options where the front, thick layer provides a large number of heavy ions to form an intense electric field after relativistic electrons are expelled and the back, thin layer provides light ions to be accelerated by the electric field. The materials and thicknesses of the bi-layer target can be optimized based on the laser parameters and acceleration requirements.

Energy Selection. A compact device for particle selection and beam modulation has been designed that utilizes a magnetic field to spread the laser-accelerated protons spatially, based on their energies and emitting angles, and apertures of different shapes to select protons within a therapeutic window of energy and angle. Such a compact device can eliminate the massive beam transportation and collimating equipment in a conventional proton therapy system. The laser-proton target assembly and the particle selection and collimating device can be installed on the treatment gantry to form a compact treatment unit, which can be installed in a conventional radiotherapy treatment room.

FIG. 1B shows a schematic diagram of the particle selection and collimation system. Theoretical proton tracks in high magnetic fields (moving from left to right) are displayed. Protons of energies within an energy range can be allowed to pass through the beam stoppers and refocused through an exit collimator. Collimators of different shapes, sizes and locations can be used to select particles of desired energies. Other protons can be stopped or scattered by the energy selection collimator so that they will not be able to reach the exit collimator. Superconducting magnets can be used to reduce the size of the device. The shielding for the whole system is designed to reduce the radiation leakage (from protons, electrons, and other radiation particles) to the level required by state regulations.

Beam Monitoring. Laser protons have a broad spectrum, which provides opportunities for selecting protons of proper energies to deliver dose distributions with desired spread out Bragg Peaks (SOBP) that is essential to treating bulky tumors. Using the particle selection device described above, proton beams of different energy spectra can be provided to realize "energy modulation." By mapping the tumor volume with an array of laser proton beams of weights, w achieve "intensity modulation" is achieved. By combining energy modulation and intensity modulation, more conformal dose distribution for radiation therapy using laser proton beams. The energy and the direction of the proton beam are varied sequentially so that the Bragg peak can cover the whole tumor volume. With a known energy, the dose rate of a conventional proton beam can be determined by a fluence monitoring chamber. For laser-accelerated protons with an energy spectrum, both the spectral shape and the fluence known to predict the dose rate and dose distribution. A solution to this problem is to install a differential chamber in the particle selection system (see FIG. 1B) so that the fluence for individual energies (different spatial locations in the energy space) can be measured. A differential chamber consists of multiple electrodes to collect ionization from different parts f the cavity volume. An integral chamber (see FIG. 1B) can be installed to monitor output of the combined beam based on the information from the differential chamber. This differential-integral chamber configuration can ensure accurate dose delivery with proper dose conformity for EIMPT using laser-accelerated proton beams.

Treatment Planning. Accurate dose calculation is needed in treatment planning for EIMPT using laser-accelerated protons because the dose distributions of small proton beamlets can be significantly affected by the beam size and heterogeneous anatomy. Patient dose calculations can be implemented using general-purpose Monte Carlo codes and fast proton dose calculation algorithms. Software can use the beam data from the PIC simulation and the patient CT to reconstruct dose calculation geometry consisting of air, tissue, lung, and bone. Based on the contours of the target volume and critical structures, the software can compute the dose distributions for plan optimization and output isodose and DVH (dose volume histogram) information for treatment plan analysis. A suitable treatment planning process for laser-accelerated proton therapy is summarized in FIG. 1C.

Treatments can be optimized for beam delivery at both low- and high-dose rate depending on the available proton numbers at required energies. Two methods include: (1) scanning beam delivery for high-dose rate (>10 Gy/min) and (2) aperture-based beam delivery for low-dose rate (<10 Gy/min). The scanning beam method uses a narrow beam (beamlet) with its Bragg peak scanned sequentially covering the whole target volume. A clear advantage of laser protons is its potential to deliver a narrow beam with a desired spectrum, which can reduce the time for depth scanning along the beam direction and therefore speed up the beam delivery by spot scanning compared with using conventional protons. The scanning beam method is specially designed to deal with the problem for low-dose output systems, which tend to be slow in providing scanned beams for EIMPT (<30 min for fractionated therapy or <60 min for stereotactic surgery). This aperture-based method is also applicable to EIMPT using conventional proton accelerators without beam scanning capabilities.

Figure 1G:
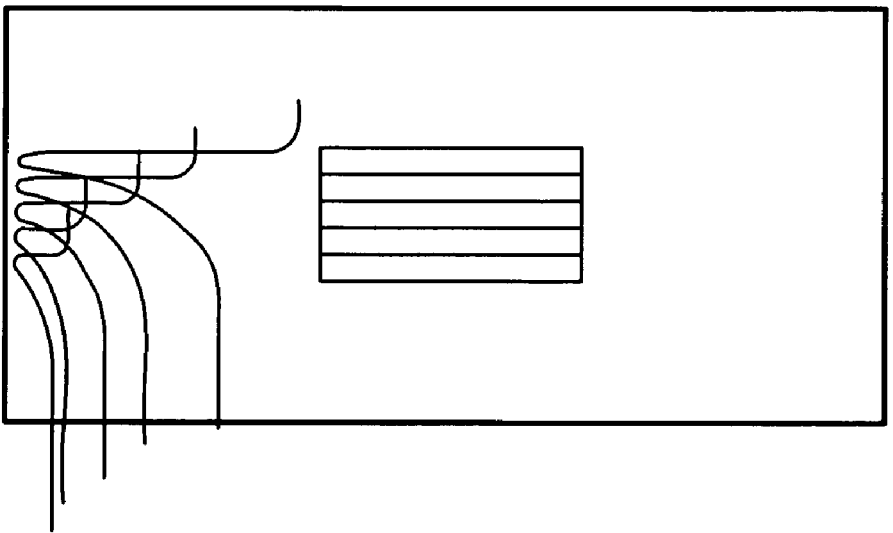
FIGS. 1G, 1H and 1I illustrate a schematic diagram for aperture-based treatment optimization for laser-proton therapy; proton beams can be collimated by apertures to conform to the cross-section of the target volume at different depths and their weights are varied to produce a SOBP to cover the whole treatment depth range (1G and 1H); if the back surface of the target is not flat (1I) a compensator can be used to ensure equal beam path length from the patient external contour to the back surface of the target so that it can be treated in the same way as for case (1H).
Figure 1H:
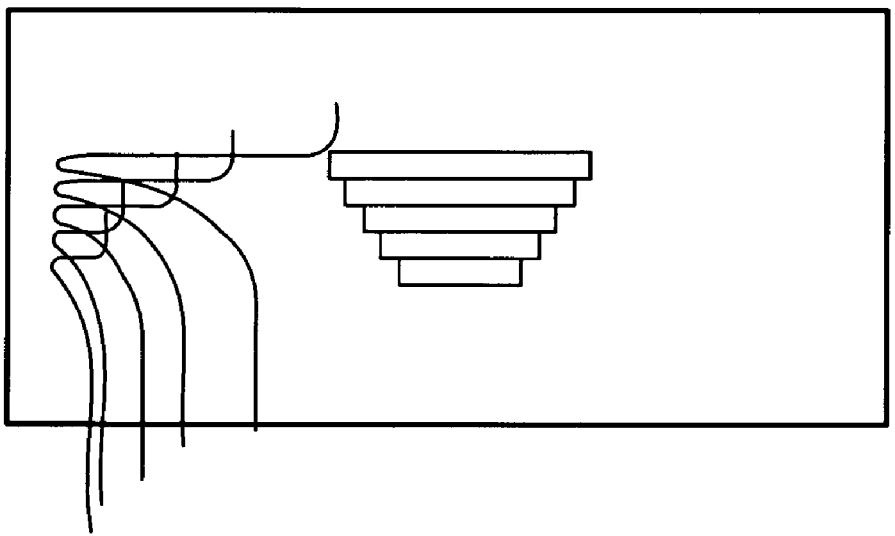
Figure 1I:
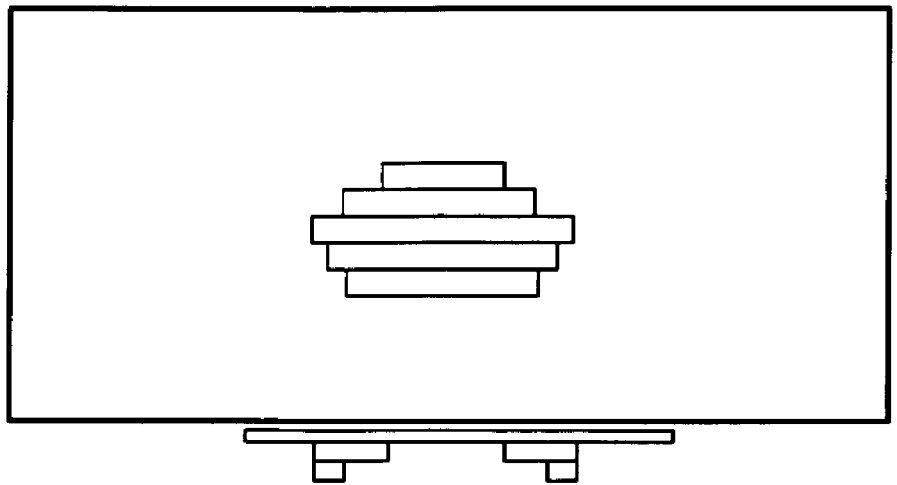

FIGS. 1G, 1H and 1I demonstrate how to use the aperture-based method to deliver a uniform dose to a target volume. For a target with a flat back surface (see FIGS. 1G and 1H), a broad proton beam is collimated with an aperture conformed to the cross-section of the tumor at a specific depth. The proton beam has a small energy spread to produce a SOBP to cover a 0.5-1.0 cm depth range. Five beams (apertures) are needed in FIGS. 1G and 1H. The mean energy and the weight of each proton beam are varied to produce a uniform dose distribution in the whole target volume. For an irregularly shaped target (see FIG. 1I), a compensator is used to provide equal beam path lengths to the back surface of the target. This can create an equivalent flat back surface for the target and then it can be treated in the same way as for the case in FIG. 1H. For a 10 cm thick target, 10 separate beams (apertures) can be used to cover the whole depth range, and, if one uses a parallel-opposed beam arrangement, a total of 20 beams can be used. For a 2-Gy/fraction treatment with a 20-min beam-on time, a laser can have a rap rate of 1 shot per min with each shot/pulse delivering up to 1 Gy at the required depth. If the dose per shot is lower, a higher rap rate can be used to maintain the dose rate of 1 Gy/min and vice versa. For the scanning method using 1 cm×1 cm beamlets, the dose rate can be a factor of 10 higher to cover a target volume with a 10 cm×10 cm cross-section (assuming each beamlet has an adequate SOBP to cover the whole target depth range).

Dosimetric Evaluation. PIC simulation results show that it is possible to accelerate protons up to 300 MeV using a laser intensity of $10^{21}$ W cm$^{-2}$ and a pulse length of 50 fs.

Figure 1J:
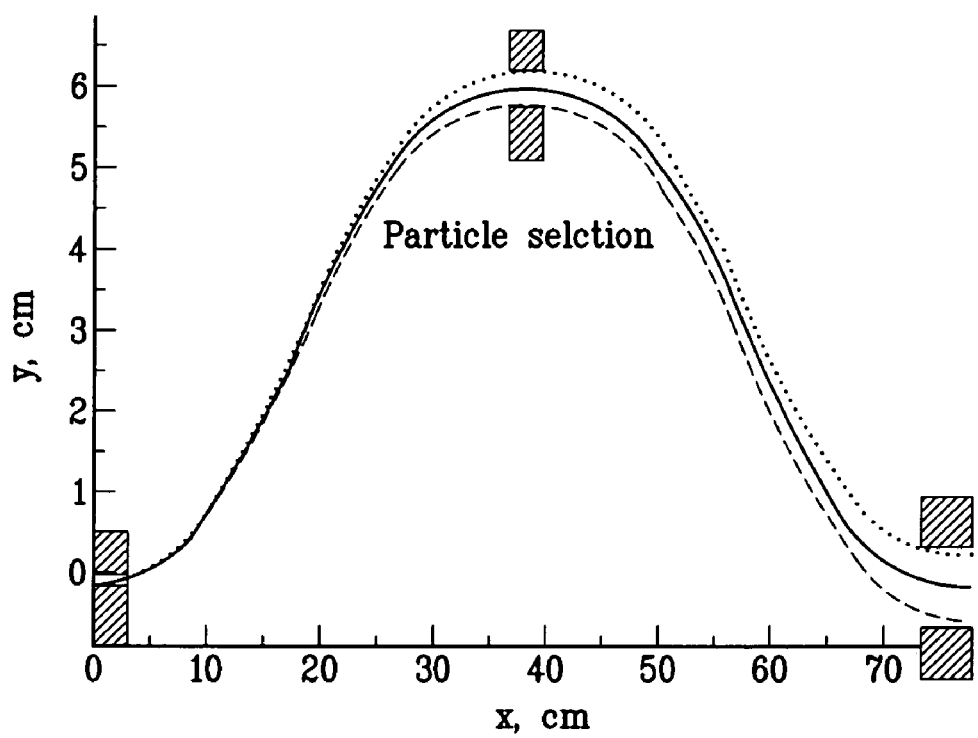
FIGS. 1J and 1K depict trajectories of laser-protons with energies about 220 MeV collimated by the particle selection aperture (1J) and depth dose curves of laser protons selected at about 70, 150 and 230 MeV (1K); dashed lines represent doses calculated based on theoretical step-function magnetic fields and solid lines represent doses calculated based on magnetic fields using superconducting magnets.
Figure 1K:
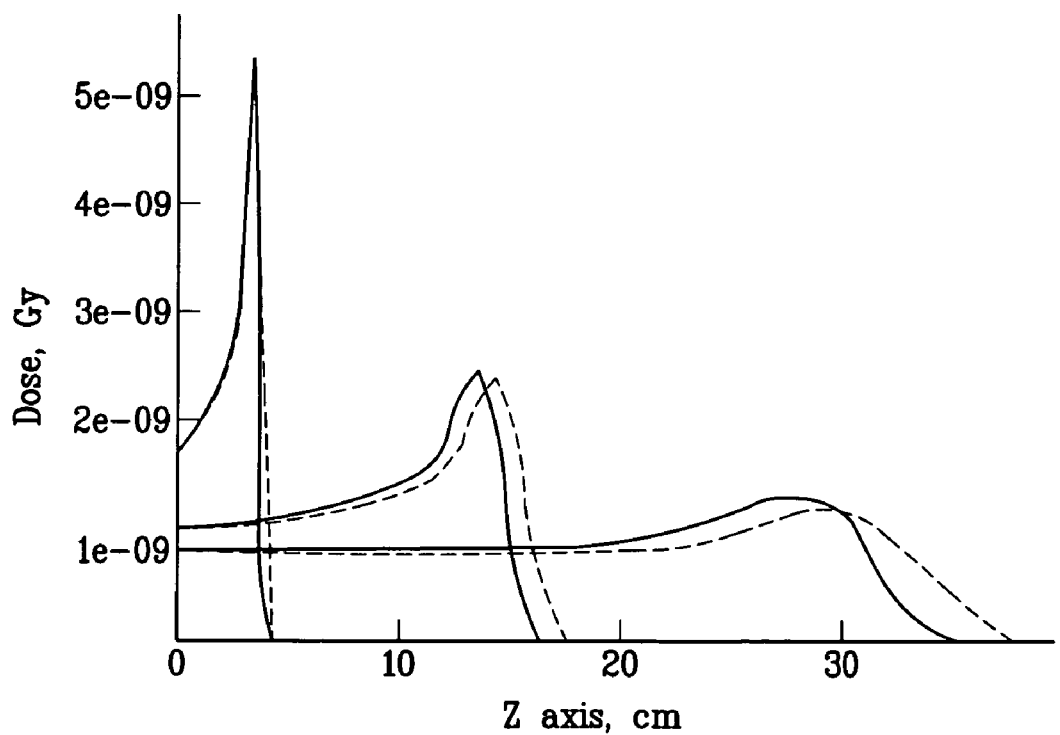
Figures 3A, 3B:
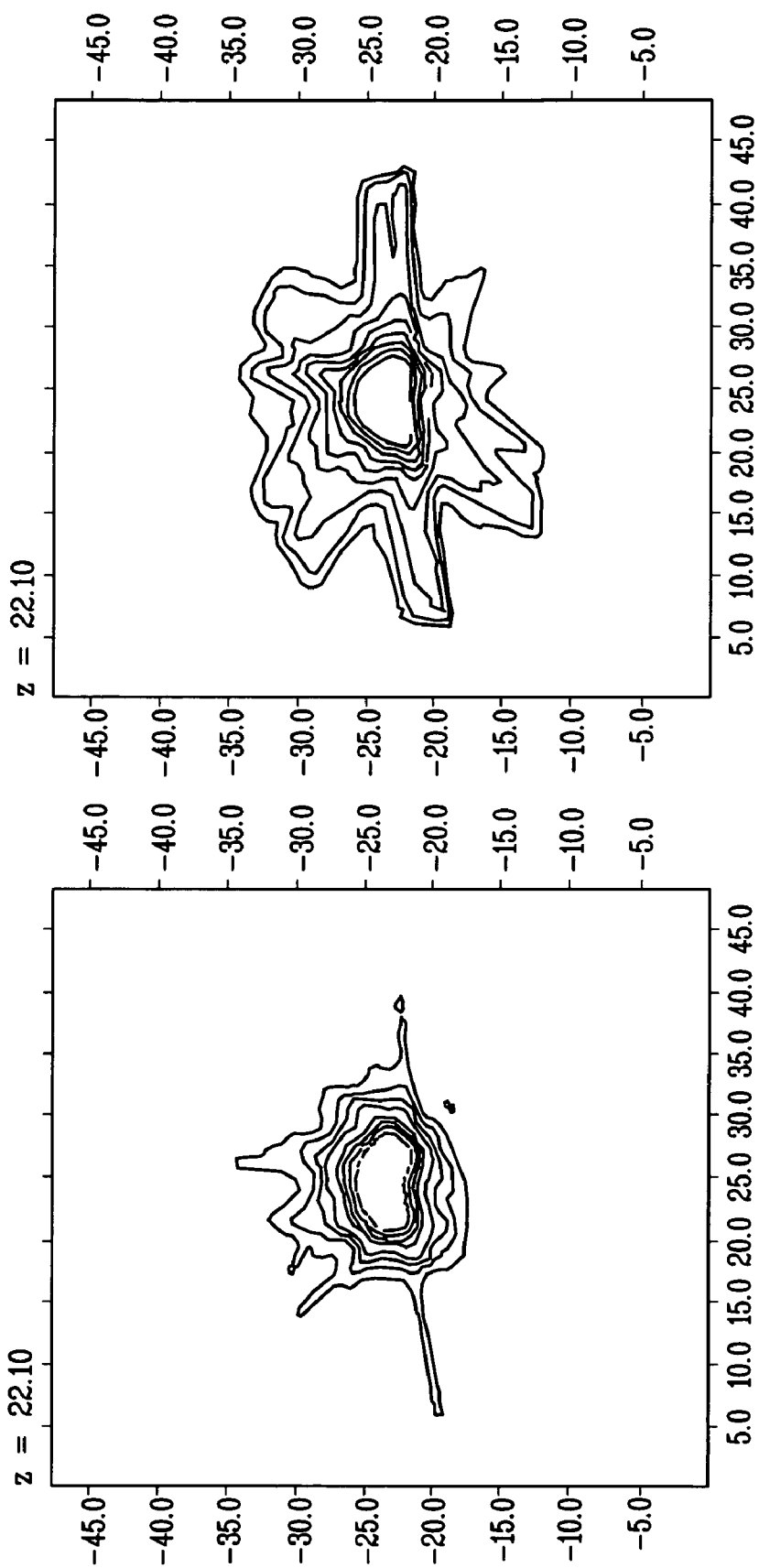
FIG. 3 provides isodose distributions for case 1 for (A) 7 field IMPT and (B) 7 field IMXT. The outermost line represents 20% of the prescription dose. The innermost line represents 100% of the prescription dose. The prescription dose is 74 Gy to 95% of the target's planning volume. The isodose distributions of 10% of the prescription dose and lower are not shown.
Figures 4A, 4B:
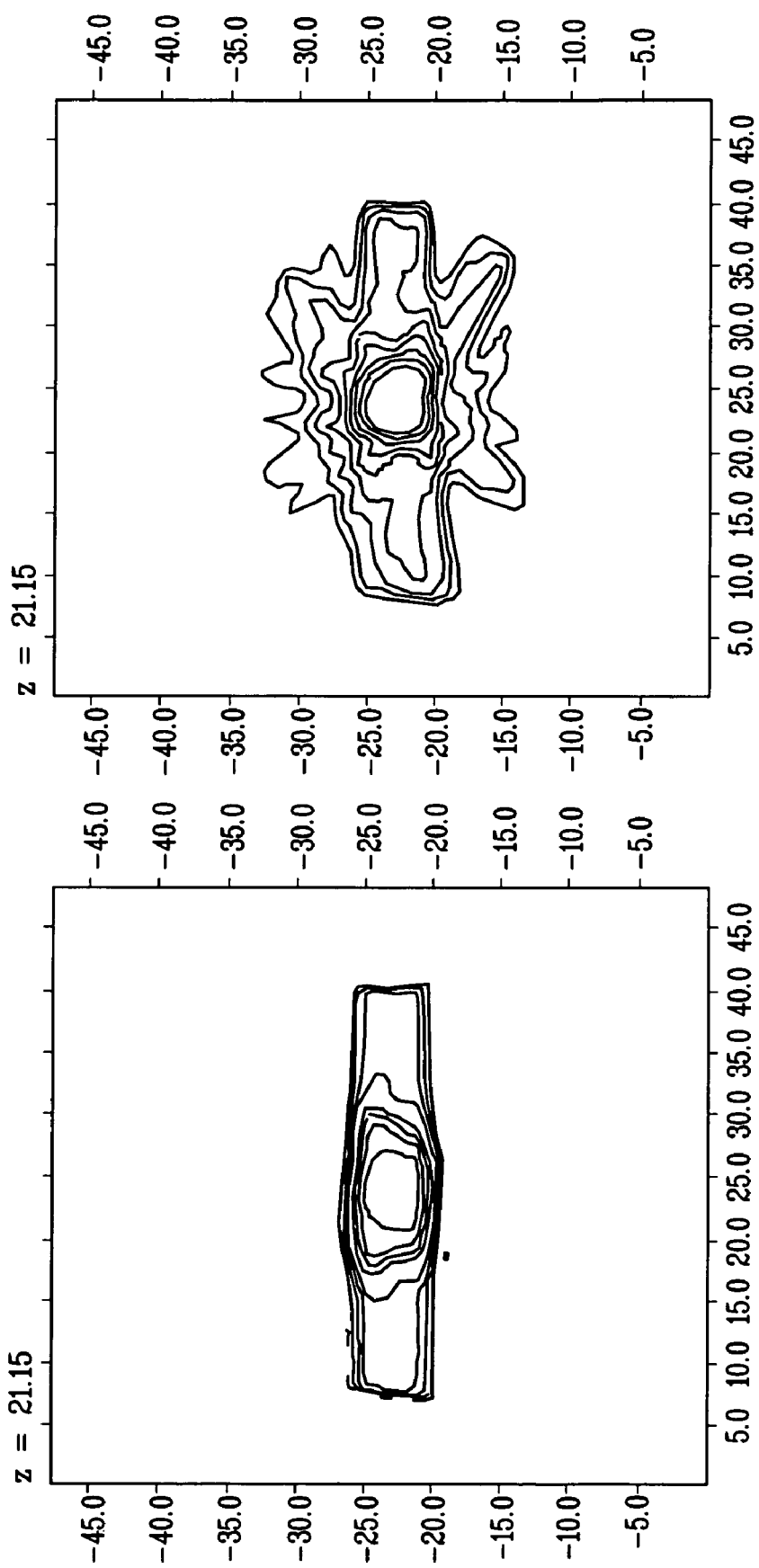
FIG. 4 provides isodose distributions for case 2 for (A) 2 field IMPT and (B) 7 field IMXT. The outermost line represents 20% of the prescription dose. The innermost line represents 100% of the prescription dose. The prescription dose is 74 Gy to 95% of the target's planning volume. The isodose distributions of 10% of the prescription dose and lower are not shown.
Figure 5:
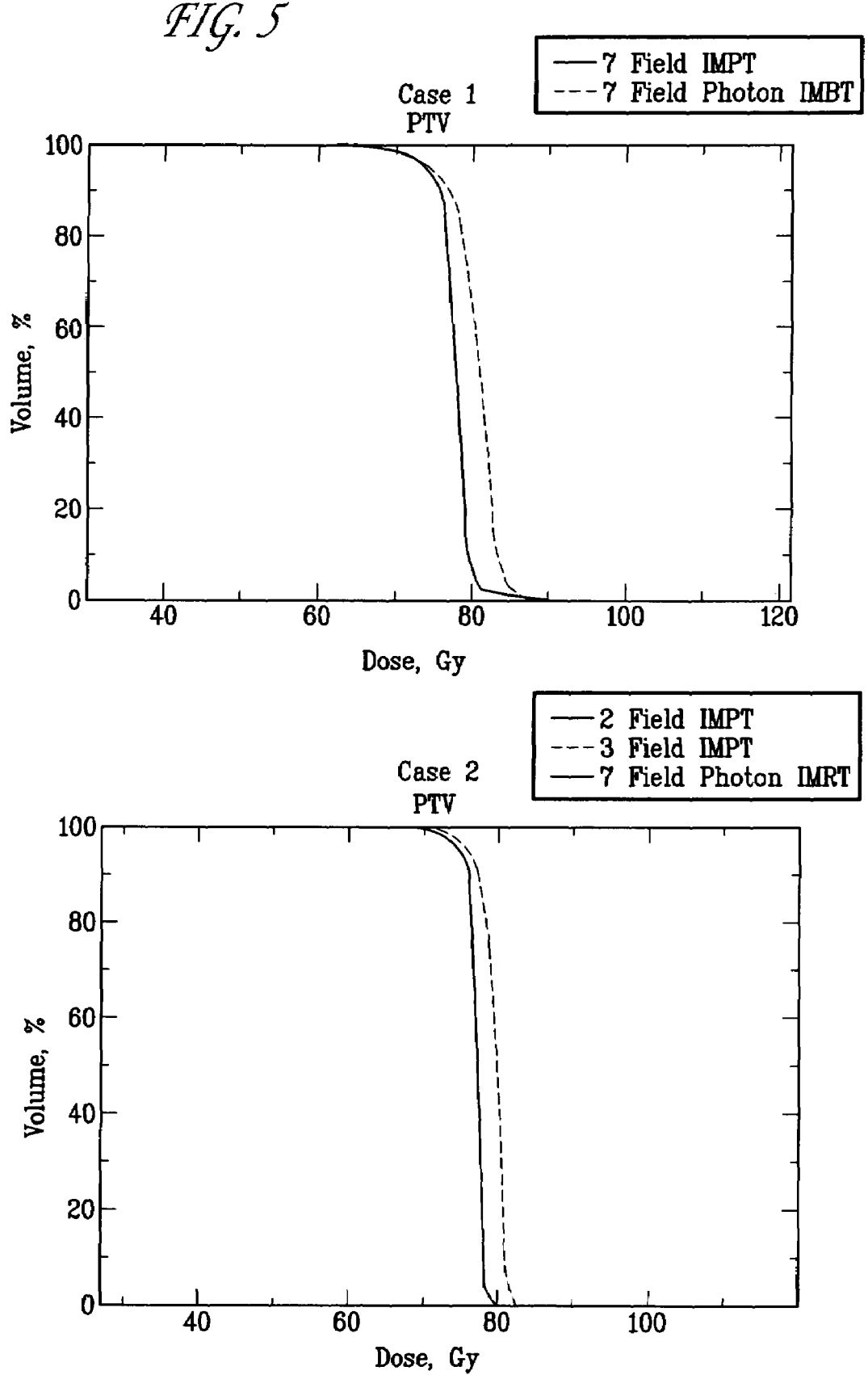
FIG. 5 provides dose-volume histograms for PTVs. The plans were normalized to 95% of the PTV's volume, which receives 100% of the prescription dose of 74 Gy.
Figure 6:
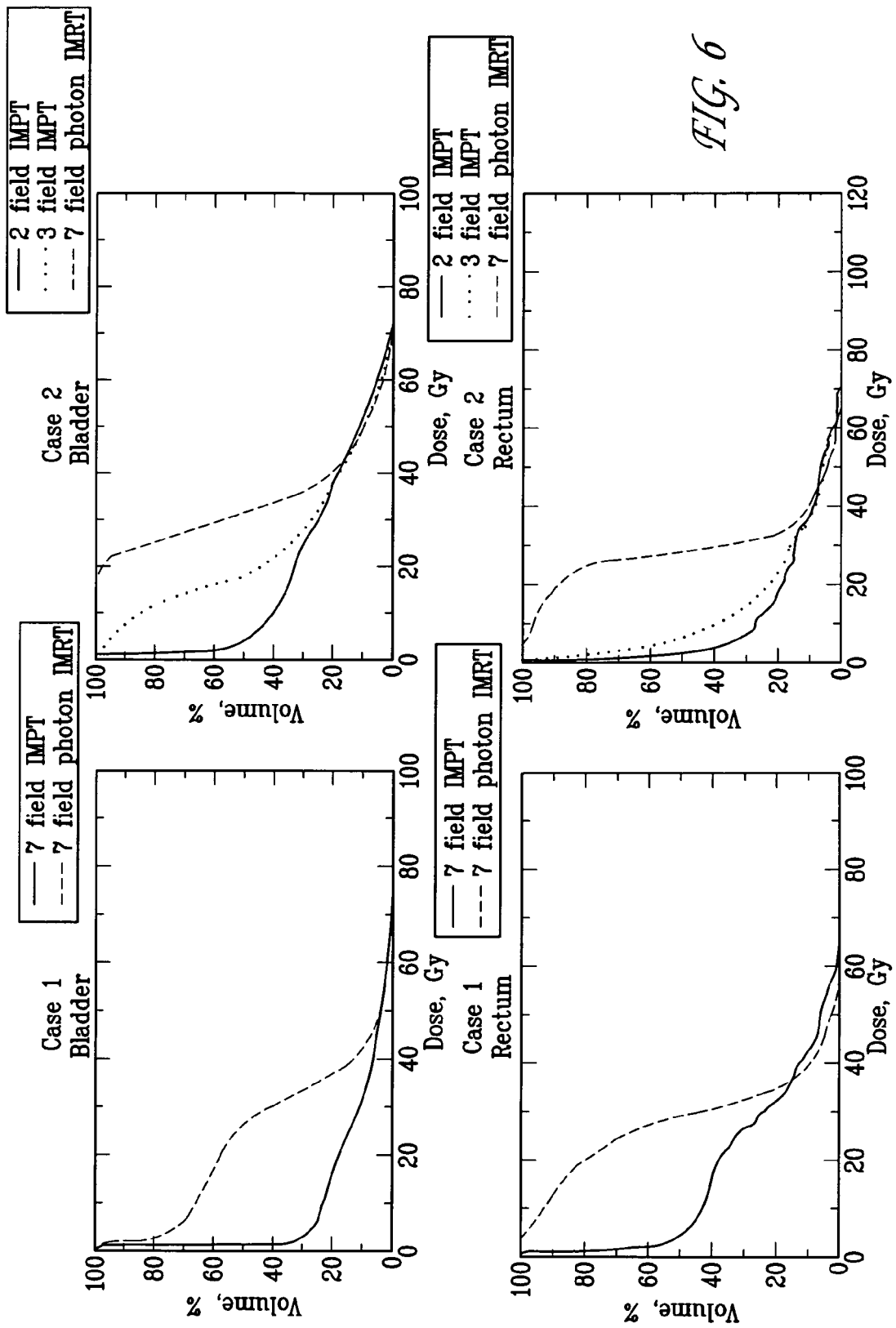
FIG. 6 provides dose-volume histograms for the rectum and bladder. The plans were normalized to 95% of the PTV's volume, which receives 100% of the prescription dose of 74 Gy.

The dose rate could be 4-20 Gy per minute depending on the treatment depth for field sizes smaller than 20 cm by 20 cm assuming a 10 Hz rap rate. The raw proton beams from a laser-driven proton accelerator can have a broad energy spectrum and angular distribution. Using a particle selection system with superconducting magnets, proton beams can be obtained with small energy spread (5-10% of the peak energy) using collimators of 1 cm×1 cm projected at 100 cm source-surface distance (SSD). FIGS. 1J and 1K show the trajectories of laser-accelerated protons with energies about 220 MeV and depth dose distributions of laser-accelerated protons of 70, 150 and 230 MeV collimated by our beam selection and collimation device. Dashed lines represent dose distributions predicted using theoretical step function magnetic fields while solid lines represent dose distributions based on realistic magnetic fields with superconducting magnets. Without being bound by any particular theory of operation, it appears that the finite size of the energy selection aperture causes each proton beam to have a small energy spread, which compromises the Bragg peak effect somewhat compared to monoenergetic protons. By combining the depth dose curves of different peak energies, a SOBP covering the desired depth range can be achieved.

What is claimed:

1. A method of generating a positive ion beam sequence for providing a prescriptive dose of high energy polyenergetic positive ions to a target volume, comprising the steps of:
  a) providing a plurality of beam angles, plan prescription, and dose constraints;
  b) providing a plan optimization process based on a beam scanning sequence;
  c) applying said beam scanning sequence to said beam angles, plan prescription and dose constraints to generate plan optimization results;
  d) comparing the plan optimization results to the plan prescription; and
  e) modulating the beam scanning sequence and iteratively repeating steps b), c) and d) until the plan optimization results are acceptable.

2. The method of claim 1, wherein the beam scanning sequence comprises, lateral scanning of beamlets, depth scanning or beamlets, 3D scanning of beamlets, or any combination thereof.

3. A method of providing a prescriptive dose of high energy polyenergetic positive ions to a target volume, comprising the steps of:
  a) providing a plurality of beam angles, plan prescription, and dose constraints;
  b) providing a plan optimization process based on a beam scanning sequence;
  c) applying said beam scanning sequence to said beam angles, plan prescription and dose constraints to generate plan optimization results;
  d) comparing the plan optimization results to the plan prescription;
  e) modulating the beam scanning sequence and iteratively repeating steps b), c) and d) until the plan optimization results are acceptable; and
  f) irradiating the target volume with a plurality of beamlets according to the plan optimization results.

4. The method of claim 3, wherein the beam scanning sequence comprises, lateral scanning of beamlets, depth scanning or beamlets, 3D scanning of beamlets, or any combination thereof.

5. A method of providing a proton radiation dose to a targeted region, comprising:
  providing a plurality of modulated polyenergetic proton beamlets; and
  irradiating said targeted region with said plurality of modulated polyenergetic proton beamlets.

6. The method of claim 5, wherein each of said polyenergetic beamlets is modulated, individually, according to at least one of: beamlet energy distribution, beamlet intensity, beamlet direction, beamlet area, or beamlet shape.

7. The method of claim 5, wherein at least a portion of said plurality of modulated polyenergetic beamlets is modulated in three dimensions.

8. The method of claim 5, wherein at least a portion of said plurality of modulated polyenergetic beamlets is modulated in intensity.

9. The method of claim 5, wherein at least a portion of said plurality of modulated polyenergetic beamlets is modulated in energy distribution.

10. The method of claim 5, wherein at least a portion of said plurality of modulated polyenergetic beamlets is modulated to irradiate the targeted region in the depth direction.

11. The method of claim 5, wherein said plurality of modulated polyenergetic beamlets are modulated to optimize the dose to minimize irradiation of organs external to said targeted region.

12. The method of claim 5, wherein said plurality of modulated polyenergetic beamlets are modulated to minimize irradiation of areas external to said targeted region.

13. The method of claim 5, wherein said plurality of modulated polyenergetic beamlets are modulated to maximize a prescriptive dose to said targeted region.

14. The method of claim 5, wherein said plurality of modulated polyenergetic beamlets are modulated to optimize the dose to minimize irradiation of critical structures and maximize a prescriptive dose to said targeted region.

15. The method of claim 5, wherein said plurality of modulated polyenergetic proton beamlets are provided by
  forming a laser-accelerated high energy polyenergetic ion beam comprising a plurality of high energy polyenergetic protons, said high energy polyenergetic protons characterized as having a distribution of energy levels;
  collimating said laser-accelerated ion beam using a collimation device;
  spatially separating said high energy polyenergetic protons according to their energy levels using a first magnetic field;
  modulating the spatially separated high energy polyenergetic protons using an aperture; and
  recombining the modulated high energy polyenergetic protons using a second magnetic field.

16. The method of claim 5, wherein each of said modulated polyenergetic proton beamlets is modulated, individually, in energy and intensity.

17. The method of claim 5, wherein said irradiating gives rise to a desired prescriptive dose to the targeted region in both longitudinal and lateral directions relative to said polyenergetic beamlets.

18. A method of providing a positive ion radiation dose to a targeted region, comprising:
  providing a plurality of modulated polyenergetic positive ion beamlets; and
  irradiating said targeted region with said plurality of modulated polyenergetic positive ion beamlets, wherein each of said polyenergetic beamlets is modulated, individually, according to at least one of: beamlet energy distribution, beamlet intensity, beamlet direction, beamlet area, or beamlet shape.

19. A method of providing a proton radiation dose to a targeted region, comprising:
providing a plurality of modulated polyenergetic proton beamlets, wherein each of said polyenergetic beamlets is modulated, individually, according to at least one of: beamlet energy distribution, beamlet intensity, beamlet direction, beamlet area, or beamlet shape; and
irradiating said targeted region with said plurality of modulated polyenergetic proton beamlets, wherein said plurality of modulated polyenergetic proton beamlets maximizes said proton radiation dose to the targeted region and minimizes said proton radiation dose to areas external to the targeted region.

20. A method of providing a prescriptive dose to a targeted region in a patient, comprising:
a) providing a plurality of polyenergetic proton beamlets; and
b) modulating said polyenergetic proton beamlets, wherein said modulating gives rise to an acceptable dose distribution to the targeted region according to the prescriptive dose in both longitudinal and lateral directions relative to said beamlets.

21. The method of claim 20, wherein said modulating step is carried out in three dimensions.

22. The method of claim 20, wherein the intensities of said polyenergetic proton beamlets are modulated.

23. The method of claim 20, wherein the energies of said polyenergetic proton beamlets are modulated.

24. The method of claim 20, wherein said polyenergetic proton beamlets are modulated to irradiate the target in the depth direction.

25. The method of claim 20, wherein said modulating step comprises optimizing the dose to minimize irradiation of organs external to said target.

26. The method of claim 20, wherein said modulating step comprises optimizing the dose to minimize irradiation of critical structures.

27. The method of claim 20, wherein said modulating step comprises optimizing the dose distribution based on a prescribed physical or biologically equivalent dose to said target.

28. The method of claim 20, wherein said modulating step comprises optimizing the dose to minimize irradiation of critical structures and optimizing the dose distribution based on a prescribed physical or biologically equivalent dose to said target.

29. The method of claim 20, wherein said polyenergetic proton beamlets are provided by
forming a laser-accelerated high energy polyenergetic ion beam comprising a plurality of high energy polyenergetic protons, said high energy polyenergetic protons characterized as having a distribution of energy levels;
collimating said laser-accelerated ion beam using a collimation device;
spatially separating said high energy protons according to their energy levels using a first magnetic field;
modulating the spatially separated high energy polyenergetic protons using an aperture; and
recombining the modulated high energy polyenergetic protons using a second magnetic field.

30. The method of claim 20, wherein the energies and intensities of said polyenergetic proton beamlets are modulated.

31. A method of providing a positive ion radiation dose, comprising:
a) providing a plurality of polyenergetic positive ion beamlets; and
b) modulating said polyenergetic positive ion beamlets, wherein said modulating gives rise to a desired dose distribution based on a prescribed dose to a target in both longitudinal and lateral directions relative to said beamlets.

32. A method of providing intensity modulated proton therapy to a targeted region in a patient, comprising:
providing a plurality of high energy positive ion beamlets;
modulating at least one of the high energy positive ion beamlets in depth relative to the patient to provide a depth-modulated beamlet;
modulating at least one of the depth-modulated beamlets in a lateral direction relative to the patient to provide a lateral-modulated beamlet; and
irradiating said targeted region with at least one of the lateral-modulated beamlets to the patient.

33. The method of claim 32, wherein said plurality of high energy positive ion beamlets comprise high energy polyenergetic positive ions.

34. The method of claim 33, wherein said plurality of high energy positive ion beamlets comprise high energy polyenergetic protons.

35. The method of claim 32, wherein said plurality of high energy positive ion beamlets comprise high energy monoenergetic positive ions.

36. The method of claim 35, wherein said plurality of high energy positive ion beamlets comprise high energy monoenergetic protons.

37. The method of claim 18, wherein said polyenergetic positive ion beamlets are provided by
forming a laser-accelerated high energy polyenergetic ion beam comprising a plurality of high energy polyenergetic positive ions, said high energy polyenergetic positive ions characterized as having a distribution of energy levels;
collimating said laser-accelerated ion beam using a collimation device;
spatially separating said high energy polyenergetic positive ions according to their energy levels using a first magnetic field;
modulating the spatially separated high energy polyenergetic positive ions using an aperture; and
recombining the modulated high energy polyenergetic positive ions using a second magnetic field.

38. The method of claim 32, wherein said polyenergetic proton beamlets are provided by
forming a laser-accelerated high energy polyenergetic ion beam comprising a plurality of high energy polyenergetic protons, said high energy polyenergetic protons characterized as having a distribution of energy levels;
collimating said laser-accelerated ion beam using a collimation device;
spatially separating said high energy polyenergetic protons according to their energy levels using a first magnetic field;
modulating the spatially separated high energy polyenergetic protons using an aperture; and
recombining the modulated high energy polyenergetic protons using a second magnetic field.

* * * * *